(12) United States Patent
Baldwin et al.

(10) Patent No.: US 10,816,190 B2
(45) Date of Patent: *Oct. 27, 2020

(54) UV LIGHT ILLUMINATED SURGICAL COVERING APPARATUS AND METHOD

(71) Applicant: FACULTY PHYSICIANS AND SURGEONS OF LOMA LINDA UNIVERSITY SCHOOL OF MEDICINE, Loma Linda, CA (US)

(72) Inventors: Dalton Duane Baldwin, Loma Linda, CA (US); Michael R. Samardzija, Colton, CA (US); Zoran Zivanovic, Loma Linda, CA (US)

(73) Assignee: FACULTY PHYSICIANS AND SURGEONS OF LOMA LINDA UNIVERSITY SCHOOL OF MEDICINE, Loma Linda, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/686,634

(22) Filed: Nov. 18, 2019

(65) Prior Publication Data

US 2020/0080718 A1    Mar. 12, 2020

Related U.S. Application Data

(63) Continuation of application No. 16/169,651, filed on Oct. 24, 2018, now Pat. No. 10,527,277, which is a
(Continued)

(51) Int. Cl.
*F21V 33/00* (2006.01)
*G05G 1/44* (2008.04)
(Continued)

(52) U.S. Cl.
CPC .......... *F21V 33/0068* (2013.01); *A61B 46/10* (2016.02); *F21V 3/04* (2013.01);
(Continued)

(58) Field of Classification Search
CPC . F21V 33/0068; A61B 46/10; F21W 2131/20; F21W 2131/202; F21W 2131/205; F21W 2131/208
See application file for complete search history.

(56) References Cited

U.S. PATENT DOCUMENTS 6,622,592 B2    9/2003  Lee
7,259,340 B2    8/2007  Blaha et al.
(Continued)

FOREIGN PATENT DOCUMENTS

EP    1 958 568    8/2008

OTHER PUBLICATIONS

Written Opinion issued in International Patent Application No. PCT/US19/57849, dated Jan. 30, 2020, ISA/US.
(Continued)

*Primary Examiner* — Robert J May
(74) *Attorney, Agent, or Firm* — Womble Bond Dickinson (US) LLP

(57) ABSTRACT

A system and method of illuminating one or more foot pedals with an optically brightened layer positioned to fluoresce responsive to activation of one or more ultraviolet (UV) illuminating devices positioned adjacent or attached to the one or more foot pedals. The optically brightened layer may include an optically brightened coating covering at least a portion of each of the one or more foot pedals, or may include an optically brightened material layer positioned to cover and protect each of the one or more foot pedals from debris or moisture during use. A friction portion may be attached to the optically brightened material layer, the friction portion being positioned adjacent a lower surface of the foot pedal when the optically brightened material layer
(Continued)

surrounds the foot pedal, the friction portion being configured to prevent sliding of the foot pedal against the floor or other surface.

20 Claims, 24 Drawing Sheets

Related U.S. Application Data continuation-in-part of application No. 16/048,260, filed on Jul. 28, 2018, now Pat. No. 10,371,370, which is a continuation of application No. 15/592,907, filed on May 11, 2017, now Pat. No. 10,060,616, which is a continuation-in-part of application No. PCT/US2015/061523, filed on Nov. 19, 2015.

(60) Provisional application No. 62/083,098, filed on Nov. 21, 2014, provisional application No. 62/338,403, filed on May 18, 2016.

(51) Int. Cl.
| | |
|---|---|
| *A61B 46/10* | (2016.01) |
| *F21V 31/00* | (2006.01) |
| *G05G 1/30* | (2008.04) |
| *F21V 23/04* | (2006.01) |
| *F21V 3/04* | (2018.01) |
| *G05G 25/04* | (2006.01) |
| *F21W 131/20* | (2006.01) |
| *A61B 17/00* | (2006.01) |
| *A61B 18/00* | (2006.01) |

(52) U.S. Cl.
CPC .............. *F21V 23/04* (2013.01); *F21V 31/00* (2013.01); *G05G 1/30* (2013.01); *G05G 1/44* (2013.01); *G05G 25/04* (2013.01); *A61B 18/00* (2013.01); *A61B 2017/00907* (2013.01); *A61B 2017/00973* (2013.01); *F21W 2131/20* (2013.01)

(56) References Cited

U.S. PATENT DOCUMENTS

| | | | |
|---|---|---|---|
| 10,060,616 | B2 | 8/2018 | Baldwin |
| 10,371,370 | B2 | 8/2019 | Baldwin |
| 2003/0047434 | A1 | 3/2003 | Hanson et al. |
| 2005/0152142 | A1 | 7/2005 | Traynor |
| 2006/0090990 | A1 | 5/2006 | Biaha et al. |
| 2007/0251849 | A1 | 1/2007 | Lo et al. |
| 2007/0268714 | A1* | 11/2007 | Chen ................. B60Q 3/12 362/510 |
| 2010/0198200 | A1 | 8/2010 | Horvath |
| 2014/0313700 | A1 | 10/2014 | Connell et al. |
| 2016/0045247 | A1 | 2/2016 | Heim et al. |
| 2017/0241637 | A1 | 8/2017 | Baldwin |
| 2019/0323704 | A1 | 10/2019 | Lee et al. |

OTHER PUBLICATIONS

International Search Report issued in International Patent Application No. PCT/US19/57849, dated Jan. 30, 2020, ISA/US.
"Surgical Drape Footswitch Cover Non-Sterile Clear Plastic 17"x15"— 100 Per Case", PDC Healthcare, http://www.pdchealthcare.com/footswitch-cover-17-wx15-d-100-cs-fsc1715.html, Oct. 18, 2014 (retrieved on Jan. 12, 2016).
"Martelli Non Slip Sewing Machine Foot Pedal Pad", Amazon.com, Inc., https://www.amazon.com/Martelli-Slip-Sewing-Machine-Pedal/dp/B004309DM4, Jul. 1, 2013 (retrieved on Jan. 12, 2016).
International Search Report and Written Opinion issued in corresponding International Application No. PCT/US2015/061523 dated Feb. 2, 2016.
Extended European Search Report issued in corresponding European Application No. 15860535.2 dated Sep. 3, 2018.

* cited by examiner

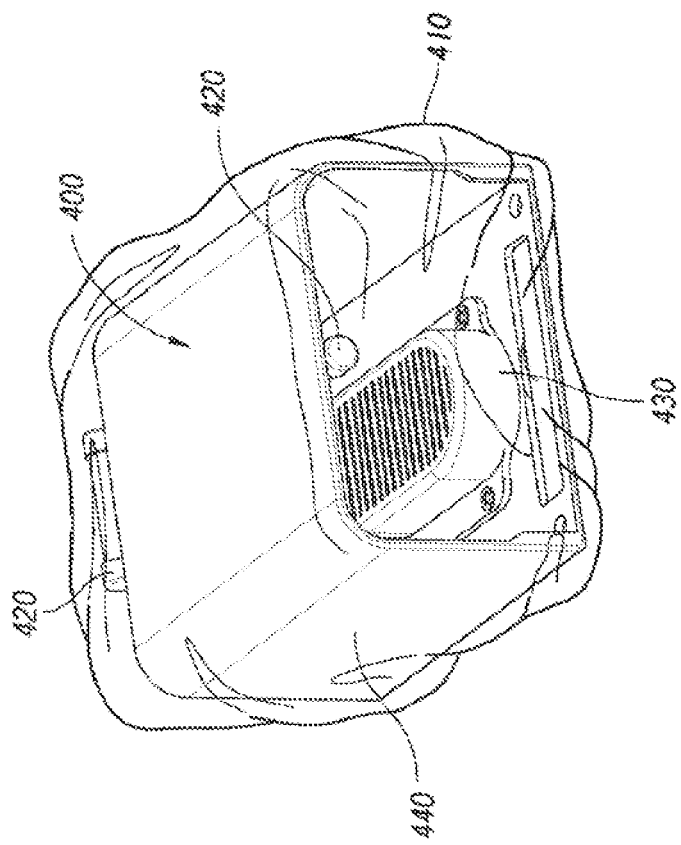
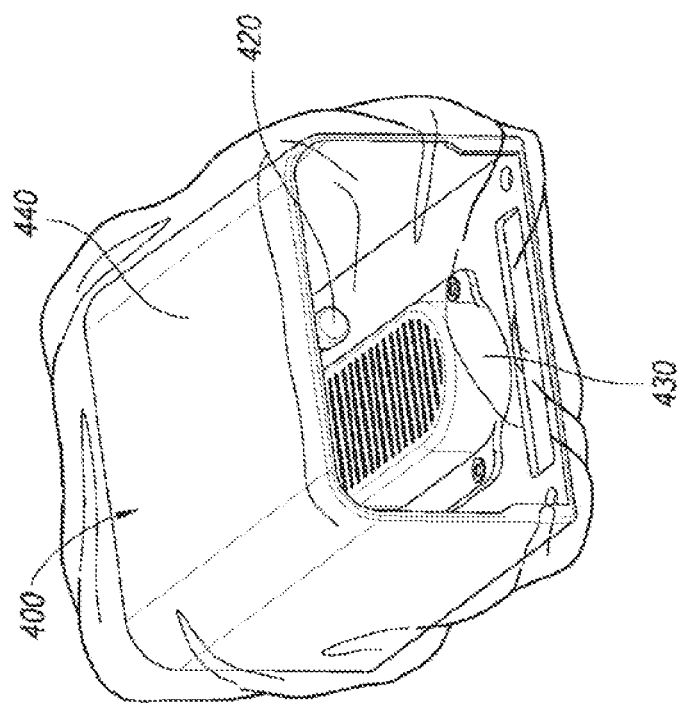
FIG.5B
FIG.5A

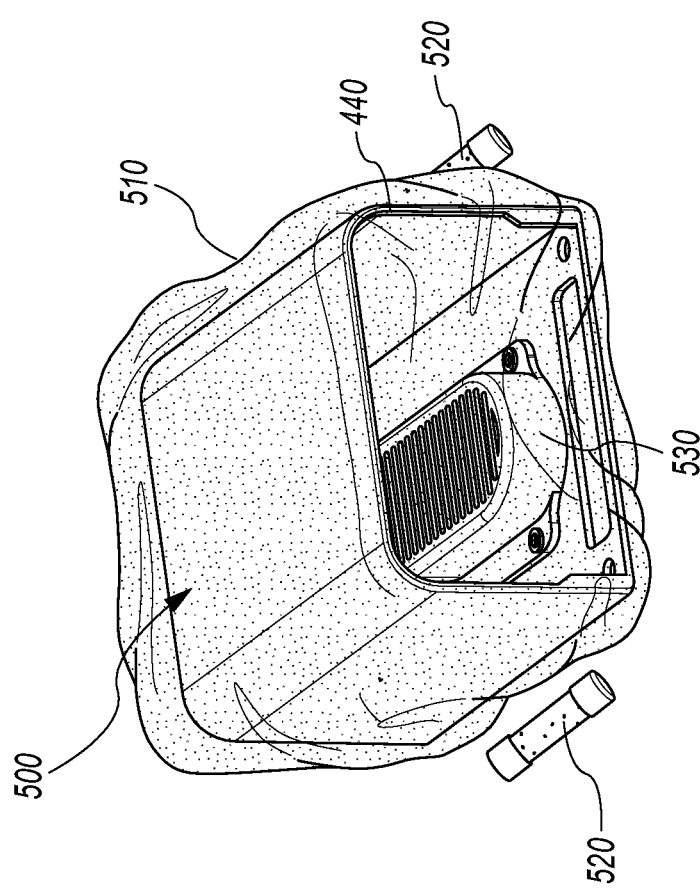

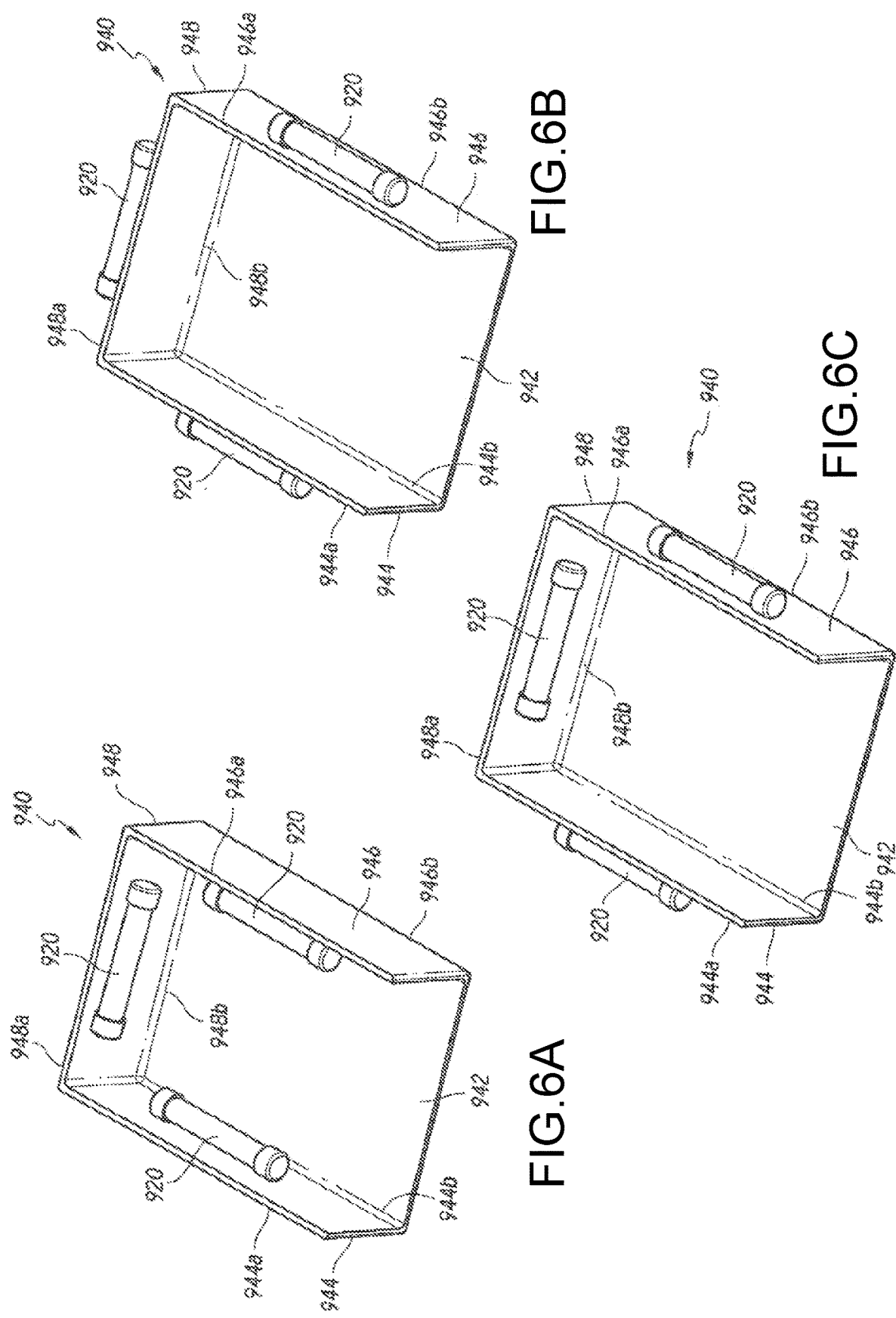

UV LIGHT ILLUMINATED SURGICAL COVERING APPARATUS AND METHOD

INCORPORATION BY REFERENCE TO ANY PRIORITY APPLICATIONS

The present application is a Continuation and claims priority to and benefit of U.S. Non-Provisional application Ser. No. 16/169,651, titled "UV LIGHT ILLUMINATED SURGICAL COVERING APPARATUS AND METHOD," filed Oct. 24, 2018, which is a Continuation in Part of U.S. Non-Provisional application Ser. No. 16/048,260, titled "ILLUMINATED PROTECTIVE COVERING FOR FOOT PEDALS," filed Jul. 28, 2018, now U.S. Pat. No. 10,371, 370, issued Aug. 6, 2019, which is a Continuation of U.S. Non-Provisional application Ser. No. 15/592,907, titled "ILLUMINATED PROTECTIVE COVERING FOR FOOT PEDALS," filed May 11, 2017, now U.S. Pat. No. 10,060, 616, issued Aug. 28, 2018, which is a Continuation in Part of International Application No. PCT/US2015/061523, titled "ILLUMINATED PROTECTIVE COVERING," filed Nov. 19, 2015, which claims priority to and the benefit of U.S. Provisional Application No. 62/083,098, titled "FOOT PEDAL LIGHTS," filed Nov. 21, 2014; the full disclosure of each of these preceding applications is incorporated herein by reference in its entirety. U.S. Non-Provisional application Ser. No. 15/592,907, titled "ILLUMINATED PROTECTIVE COVERING FOR FOOT PEDALS," filed May 11, 2017, now U.S. Pat. No. 10,060,616, issued Aug. 28, 2018, also claims priority to and the benefit of U.S. Provisional Application No. 62/338,403, titled "ILLUMINATED PROTECTIVE COVERING," filed May 18, 2016, the full disclosure of which also is incorporated herein by reference in its entirety.

BACKGROUND

Field

The present disclosure relates to illuminated coverings and associated methods that may be used with surgical devices.

Description of the Related Art

Foot pedals are used in a variety of environments, including surgical environments. Surgical devices are used in an operating room during surgical procedures. The surgical devices may include foot pedals that are frequently placed on the floor beneath the patient and may be depressed to activate and operate the surgical device.

SUMMARY

Certain aspects of the present disclosure are directed toward an illuminated covering for a surgical device, for example a foot-activated surgical device that may be used in an operating room during surgery, and associated methods. An embodiment of an apparatus and method, for example, may be an ultraviolet (UV) light illuminated covering for a surgical device for use in an operating room during surgery.

Foot pedals may be used in many different applications and are frequently used to operate devices and/or machinery. In some implementations, the foot pedals may be used for playing musical instruments (such as pianos, keyboards, drums, and guitars). In some implementations, the foot pedals may be used with sound equipment, e.g., to control amplifiers, synthesizers, laptops, etc., in sound booths, DJ booths, or other similar environments. In some implementations, the pedals may be used with movie equipment, e.g., to control sound equipment or lighting equipment. In some implementations, the pedals may be used for the operation of motor vehicles. In some implementations, the foot pedals may be used with portable devices such as sewing machines. In some implementations, the foot pedals described herein may be used during medical procedures, such as with surgical foot pedals. Each of these pedals may be placed on the floor near the foot of the user.

During a surgical procedure, a surgeon may have different types of foot pedals to operate one of the many pieces of equipment during surgery. As an example, in urology, a first foot pedal may be used to operate a laser to break stones and treat tumors, a second foot pedal may be used to perform electrocautery to trim out prostate and bladder tumors, a third foot pedal may be used to operate a C-arm, and a fourth foot pedal may be used to operate an ultrasonic lithotripsy device. Each of these pedals may be placed on the floor beneath the operating table.

Furthermore, many surgical procedures, such as those involving endoscopy, laparoscopy, and robotic devices, as well as other, non-surgical uses of foot pedals, can require a darkened environment or areas with low light.

The darkened environment and the location of the foot pedals create a situation that can result in human error as the inability to easily and properly locate the proper foot pedal can cause the wrong pedal to be depressed and the wrong device to be activated. In surgical contexts, operating the wrong foot pedal can result in significant patient and surgeon harm. As well, the darkened environment can cause the user to have difficulty locating the foot pedal, which can lead to missing or kicking of the foot pedal.

To reduce surgeon or other user error, the foot pedal may be provided with an embodiment of an illuminated cover including an optically brightened layer that, when illuminated, allows the surgeon or other user to easily identify the appropriate foot pedal to be used. For example, objects or materials having an optically brightened exterior may fluoresce when exposed to ultraviolet (UV) light, and an example of such a UV light may be what is known as a blacklight. In some embodiments, this optically brightened exterior may include a white exterior, though other colors may also be optically brightened so as to fluoresce responsive to activation of UV light. In some embodiments, this optically brightened layer may include an optically brightened material layer, or in other embodiments may include an optically brightened coating. In embodiments where the optically brightened layer includes an optically brightened material layer, the optically brightened material layer may include an illuminated protective cover that may also protect the foot pedal from moisture damage as well as debris generated from the environment, such as during a surgical procedure. In some embodiments, the foot pedal and/or the optically brightened material layer or coating may be color-coded to help the surgeon or other user identify the purpose of each pedal as well as the proper placement of the foot. In some embodiments, a foot pedal may have a number of different actuators (e.g., pedals, buttons, etc.). The illuminated cover may help the surgeon or other user identify the location of each of the different actuators.

The illumination devices and illuminated cover may be separately attached such that the surgeon may easily adapt the illuminated cover for any device being used with a foot pedal. Further, the illumination devices and/or the illuminated cover may be disposable and configured to be used on a foot pedal of any size or shape. Disposability, for example, may be important for maintaining a clean surgical environment.

In some embodiments, the illuminated cover may further include a frame to provide additional protection to the foot pedal and for elevated lighting of the foot pedal. The illuminated cover may also include an attachable friction surface to prevent the covered foot pedal from slipping against a surface.

Accordingly, the present disclosure is directed to a system for illuminating one or more foot pedals, according to an embodiment. In an embodiment, the system may include one or more foot pedals, each of the foot pedals: being configured to transition from an initial position to a depressed position; being positioned to activate a function of the foot pedal when in the depressed position; and having an upper surface and a lower surface, the lower surface being adapted to be positioned on a floor or other surface.

In an embodiment, the system may further include one or more ultraviolet (UV) illuminating devices positioned to illuminate light therefrom and onto the one or more foot pedals. An optically brightened layer may be positioned to cover at least a portion of the upper surface of each of the one or more foot pedals, and may be positioned to fluoresce responsive to activation of the UV light illuminated from the one or more UV illuminating devices, so as to provide visibility for the one or more foot pedals.

In an embodiment, the optically brightened layer may include an optically brightened material layer in the form of an illuminated protective cover, and the illuminated protective cover may be connected to each of the one or more foot pedals and substantially cover the upper surface and the lower surface of each of the one or more foot pedals and the plurality of illuminating devices. The illuminated protective cover may be positioned to protect each of the one or more foot pedals from debris, and may be sufficiently flexible to substantially conform to a shape of each of the one or more foot pedals.

In an embodiment, one or more of the UV illuminating devices may be connected to at least a portion of a perimeter of each of the one or more foot pedals.

In another embodiment, one or more of the UV illuminating devices is located at a height above a top surface of each of the one or more foot pedals.

In another embodiment, one or more of the UV illuminating devices may be positioned adjacent to the one or more foot pedals.

In an embodiment, the optically brightened layer may include an optically brightened coating.

In another embodiment, the optically brightened layer may include an optically brightened material layer, the optically brightened material layer being positioned about each of the one or more foot pedals so as to protect each of the one or more foot pedals from at least one of debris and moisture; and including a friction portion positioned adjacent the lower surface of each of the one or more foot pedals so as to reduce sliding of each of the one or more foot pedals against the floor or other surface.

In an embodiment, the system may include a frame positioned to receive the one or more foot pedal.

In an embodiment, the frame may have a bottom wall; first and second walls extending upward from opposite lateral sides of the bottom wall; and a third wall extending between the first and second walls and along a side of the bottom wall.

In an embodiment, the optically brightened material layer may be further connected to the frame.

In an embodiment, each of the one or more UV illuminating devices may be positioned on one or more of an inside surface of the frame and an outside surface of the frame.

In an embodiment, the system may include a switch for activating and deactivating the one or more UV illuminating devices.

In an embodiment, each of the one or more UV illuminating devices may be removably attached to one or more of the one or more foot pedal and the optically brightened material layer.

In an embodiment, each of the one or more UV illuminating devices may be located at a height above a top surface of each of the one or more foot pedals.

The present disclosure is also directed to an illuminated protective covering to cover and illuminate one or more foot pedals, according to an embodiment. In an embodiment, the covering may include a frame positioned to receive the one or more foot pedals, the frame including a bottom wall; first and second walls extending upward from opposite lateral sides of the bottom wall; and a third wall extending between the first and second walls and along a side of the bottom wall.

In an embodiment, the covering may include one or more ultraviolet (UV) illuminating devices to illuminate light therefrom, one or more of the UV illuminating devices being attached to one or more of the walls of the frame.

In an embodiment, the covering may include an optically brightened material layer positioned to cover the frame to provide protection from debris, the optically brightened material layer being sufficiently flexible to substantially conform to the one or more foot pedals; and a friction portion positioned on the covering such that the friction portion is adjacent a lower surface of each of the one or more foot pedals when the cover is positioned on the one or more foot pedals, the friction portion positioned to prevent sliding of the one or more foot pedals against a floor or other surface.

The present disclosure is further directed to a method for illuminating one or more foot pedals, according to an embodiment. In an embodiment, the method may include covering at least a portion of an upper surface of the one or more foot pedals with an optically brightened layer.

In an embodiment, the method further may include positioning one or more ultraviolet (UV) illuminating devices to illuminate light therefrom and onto the optically brightened layer and the one or more foot pedals, such that the optically brightened layer fluoresces responsive to activation of the one or more UV illuminating devices and provides visibility for the one or more foot pedals.

In an embodiment, the optically brightened layer may be sufficiently flexible to substantially conform to a shape of the one or more foot pedals.

In an embodiment, the method may include covering at least a portion of the upper surface of the one or more foot pedals with an optically brightened coating.

In an embodiment, the method may include covering upper and lower surfaces of the one or more foot pedals with the optically brightened material layer, the optically brightened material layer being positioned to protect the one or more foot pedals from moisture and other debris.

Other aspects and features of the present disclosure will become apparent to those of ordinary skill in the art after reading the detailed description herein and the accompanying figures.

BRIEF DESCRIPTION OF DRAWINGS

Various embodiments are depicted in the accompanying drawings for illustrative purposes, and should not be interpreted as limiting the scope of the embodiments. Furthermore, various features of different disclosed embodiments may be combined to form additional embodiments, which are part of this disclosure:

FIGS. 5A-5M illustrate an embodiment of a protective frame that may be used with an illuminated protective covering, wherein the protective frame is disposed about a foot-activated device and the illuminating device may be located in a number of different locations.

FIGS. 6A-6C illustrate another embodiment of the protective frame with a plurality of illuminating devices attached.

DETAILED DESCRIPTION

Figure 1A:
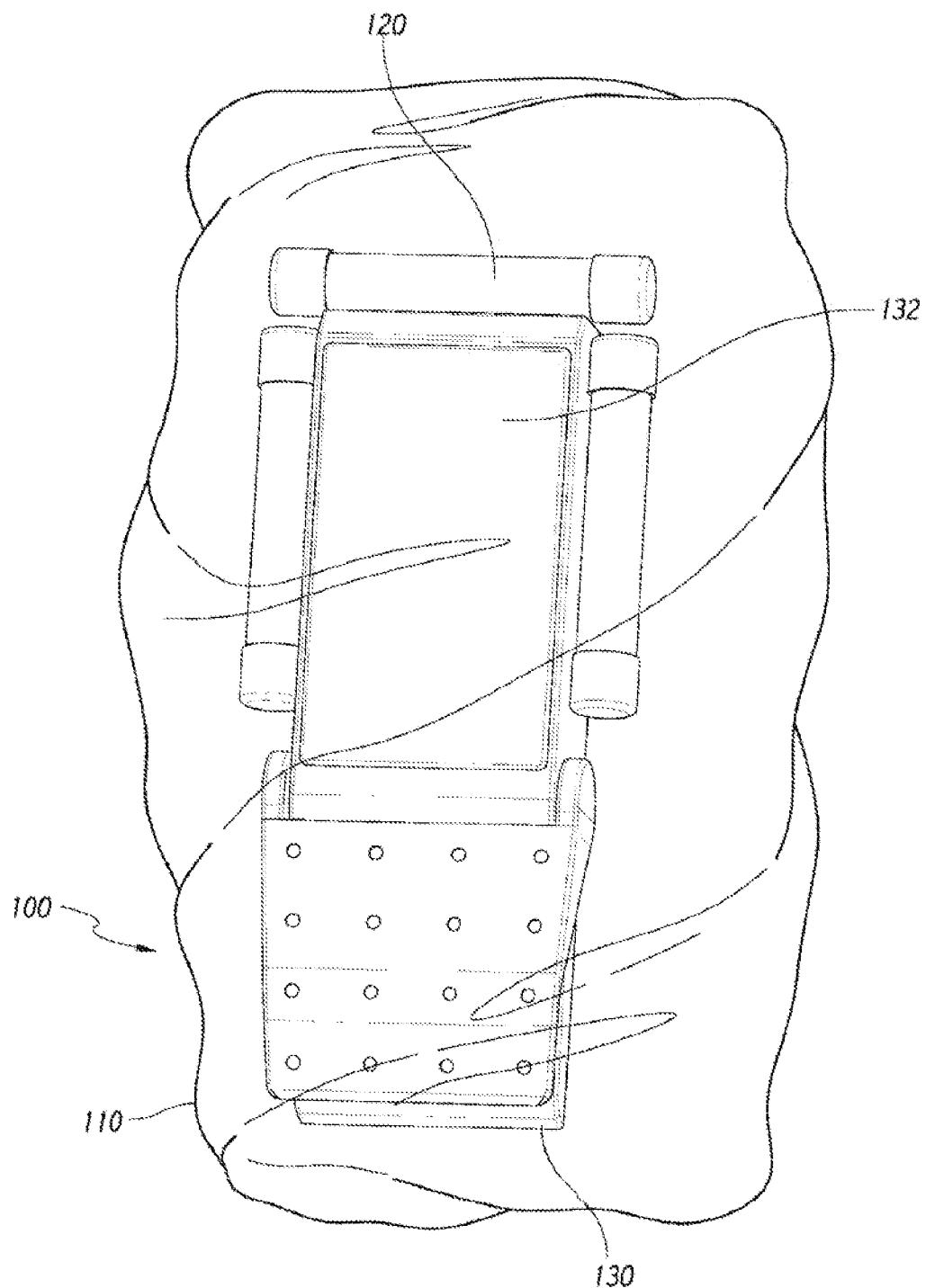
FIGS. 1A-1F illustrate an embodiment of an illuminated protective covering for a foot-activated device with a single foot pedal.

Various illuminated device covers, assemblies, and methods are disclosed to illustrate various examples that may be employed to achieve one or more desired improvements. For purposes of presentation, certain embodiments are disclosed with respect to a surgical device with a foot pedal, but the disclosed invention may be used in other contexts as well. Indeed, the described embodiments are examples only and are not intended to restrict the general disclosure presented and the various aspects and features of this disclosure. The general principles described herein may be applied to embodiments and applications other than those discussed herein without departing from the spirit and scope of the disclosure. This disclosure should be afforded the widest scope consistent with the principles and features that are disclosed or suggested herein.

Although certain aspects, advantages, and features are described herein, it is not necessary that any particular embodiment include or achieve any or all of those aspects, advantages, and features. For example, some embodiments may not achieve the advantages described herein, but may achieve other advantages instead. No feature, component, or step is necessary or critical.

Overview

The present disclosure is directed toward an illuminated cover that may be used in connection with a foot pedal of a foot-activated device, and in an embodiment may be placed over a surgical foot pedal. In some embodiments, the illuminated cover may include an optically brightened coating positioned to cover at least a portion of an upper surface of the foot pedal. In other embodiments, the illuminated cover may include an optically brightened material layer positioned to cover and protect at least a portion of the upper surface of the foot pedal. According to various embodiments, one or more illuminating device may be positioned adjacent or attached to the foot pedal. In some embodiments, the illuminating device may include an ultraviolet (UV) illuminating device, positioned to illuminate light therefrom and onto the foot pedal and the optically brightened layer, such that the optically brightened layer fluoresces responsive to activation of the illumination of the UV illuminating device so as to provide visibility for the foot pedal. As described below, in examples where the illuminated cover is an optically brightened material layer, the optically brightened material layer may be positioned to form a protective cover that may include a support structure (e.g., a frame or sheet of material) and at least one illuminating device, according to an embodiment. For example, the optically brightened material layer may include a protective sheet that may be secured around the foot pedal to protect the foot pedal from damage from moisture or other debris generated from the environment, such as from a surgical procedure in an embodiment (see, e.g., FIGS. 1A-1D, 2A-2B, 3A-3B, 4A-4B, and 5A-5M). In some examples, the protective sheet may be at least partially optically transmissive to allow the foot pedal to be easily visible. In an embodiment, the foot pedal may be positioned within a frame that supports the at least one illuminating device (see, e.g., FIGS. 6A-6C). In some examples, the illuminated cover may include an optically brightened coating, which may be applied to one or more surfaces of the foot pedal (see, e.g., FIGS. 8A-8D) or to one or more surfaces of a frame surrounding the foot pedal (see, e.g., FIGS. 9A-9D).

One or more UV illuminating devices may be positioned adjacent or connected to the foot pedal, the frame, and/or the illuminating cover so as to cause the optically brightened layer positioned over the foot pedal and/or frame to fluoresce, so as to enable a user, such as a surgeon, to easily identify and access the appropriate foot pedal, for example during surgery. In some configurations, the illuminated cover and/or the one or more illuminating devices may be customized for foot pedals having specific sizes, such as specific surgical foot pedal devices. In other configurations, there may be a "one-size fits all" kit where the illuminated cover and the illuminating device(s) may be used for any number of different foot pedal designs. In either configuration, the plurality of illuminated devices may be removably or permanently attached to the foot pedal, positioned adjacent to or above the foot pedal, and/or attached to the optically brightened layer. As described further below, the system may include a separate frame structure for receiving the surgical foot pedal, which may be attached to or retain one or more illuminating devices. The frame may be configured to provide the foot pedal with additional protection or to allow the placement of the illuminating devices at additional elevations and/or angles.

In some embodiments, where the illuminated cover is an optically brightened coating, one or more UV illuminating devices may be attached to the foot pedal or may be positioned adjacent to or above the foot pedal so as to illuminate light therefrom and onto the optically brightened coating and the one or more foot pedals, causing the optically brightened coating to fluoresce, thereby allowing for visualization of the one or more foot pedals. The optically brightened coating may include an optically brightened liquid or spray paint, for example. In some examples, this optically brightened coating may include a white paint or other white coating material, as will be readily understood by one having ordinary skill in the art. In some embodiments, the optically brightened coating may be provided having various fluorescent colors such that different foot pedals may be separately identified according to distinctly fluorescing colors.

Although the following description of the illuminated cover will be discussed in relation to a foot pedal, the present disclosure is not intended to be limiting to foot pedals. The described illuminated cover may be used with any number of compressible devices (e.g., foot switches, foot buttons, etc.) that are used frequently and need to be protected from the environment, for example for use in surgical operating rooms.

Protective Cover and Illuminating Device(s)

Figure 1B:
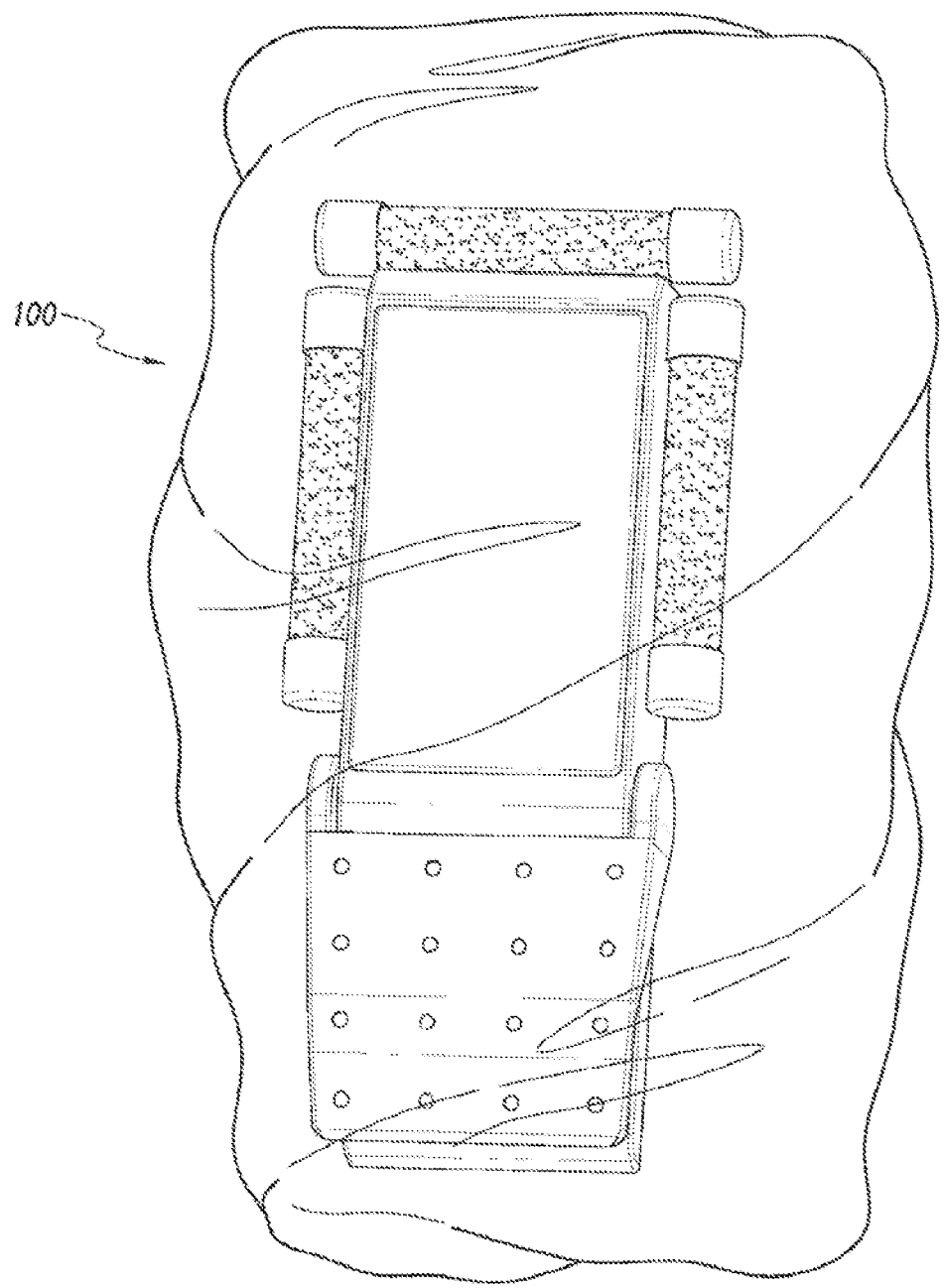
Figure 1D:
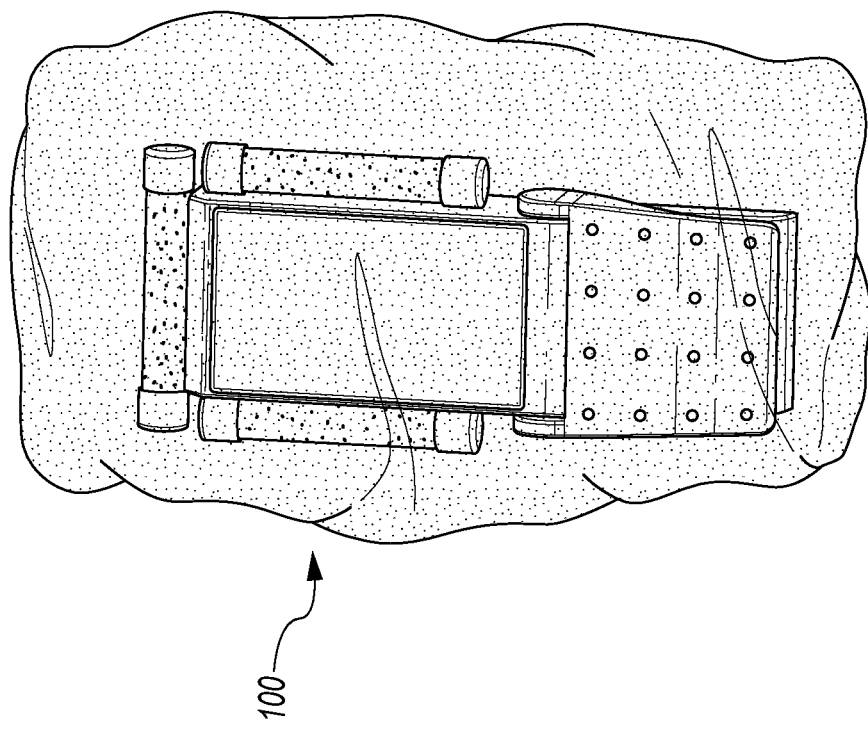
Figure 1C:
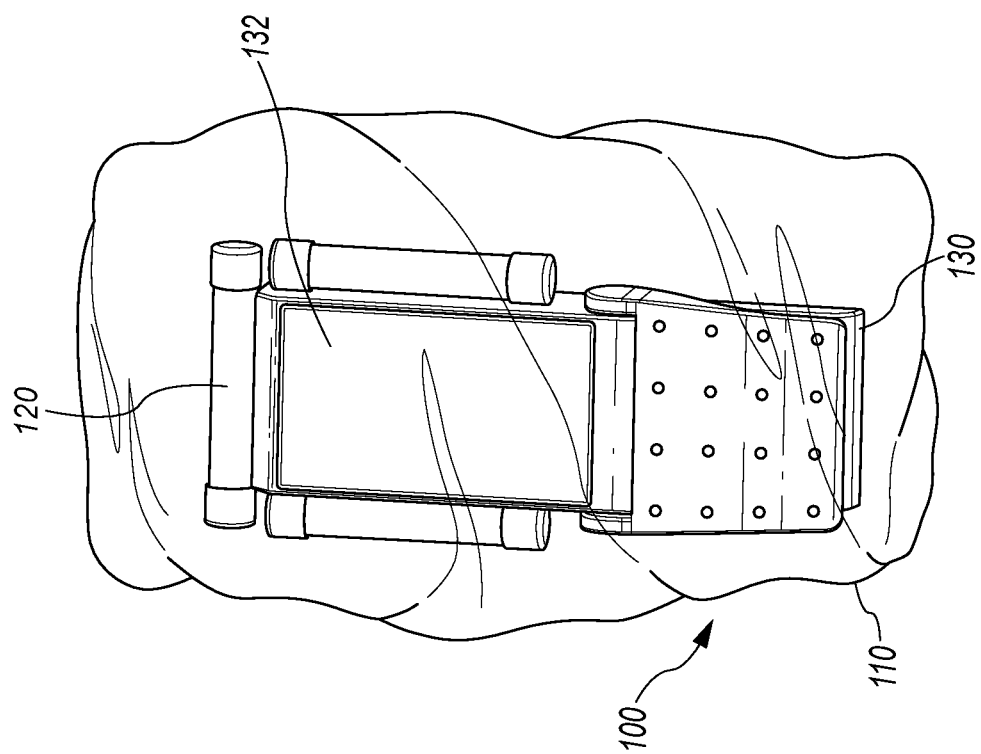
Figure 1F:
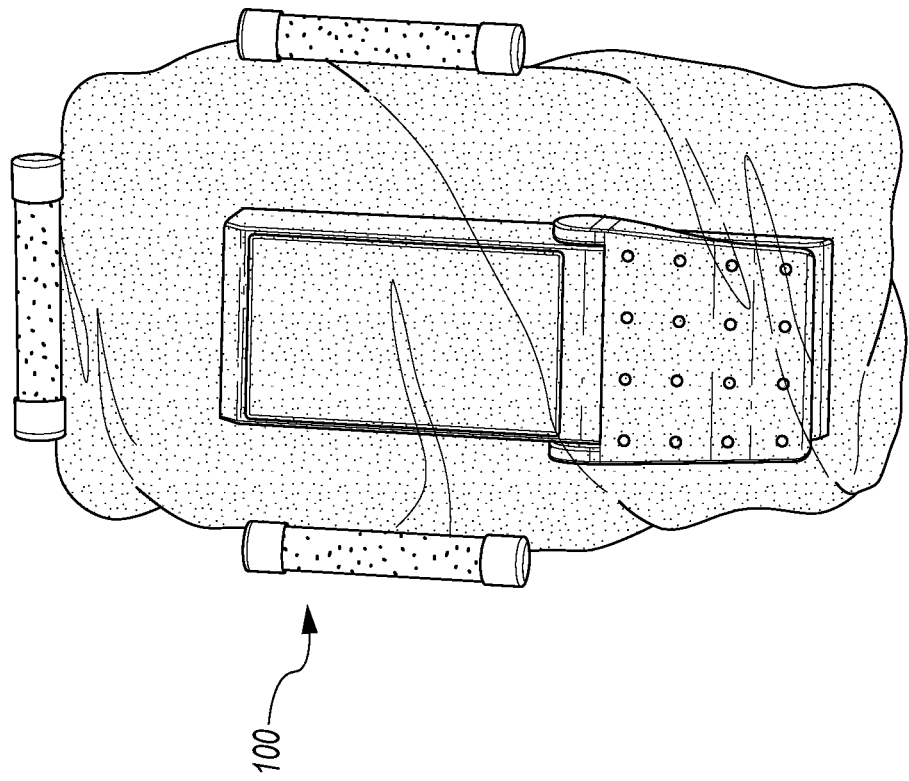
Figure 1E:
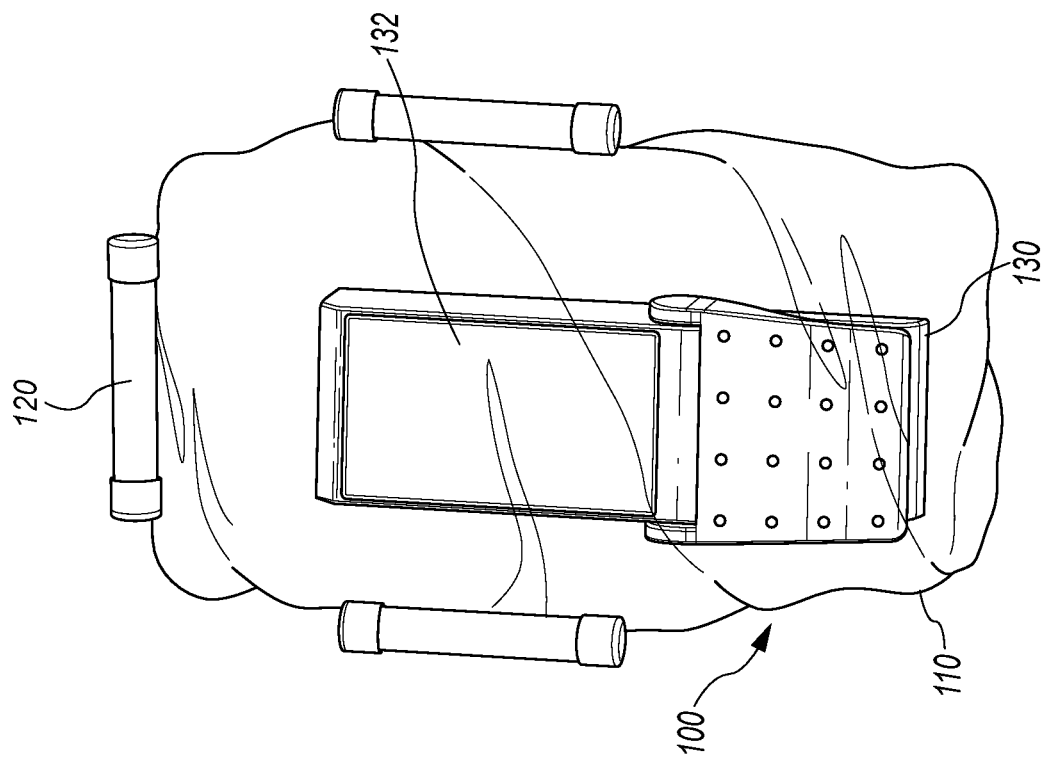
Figure 2A:
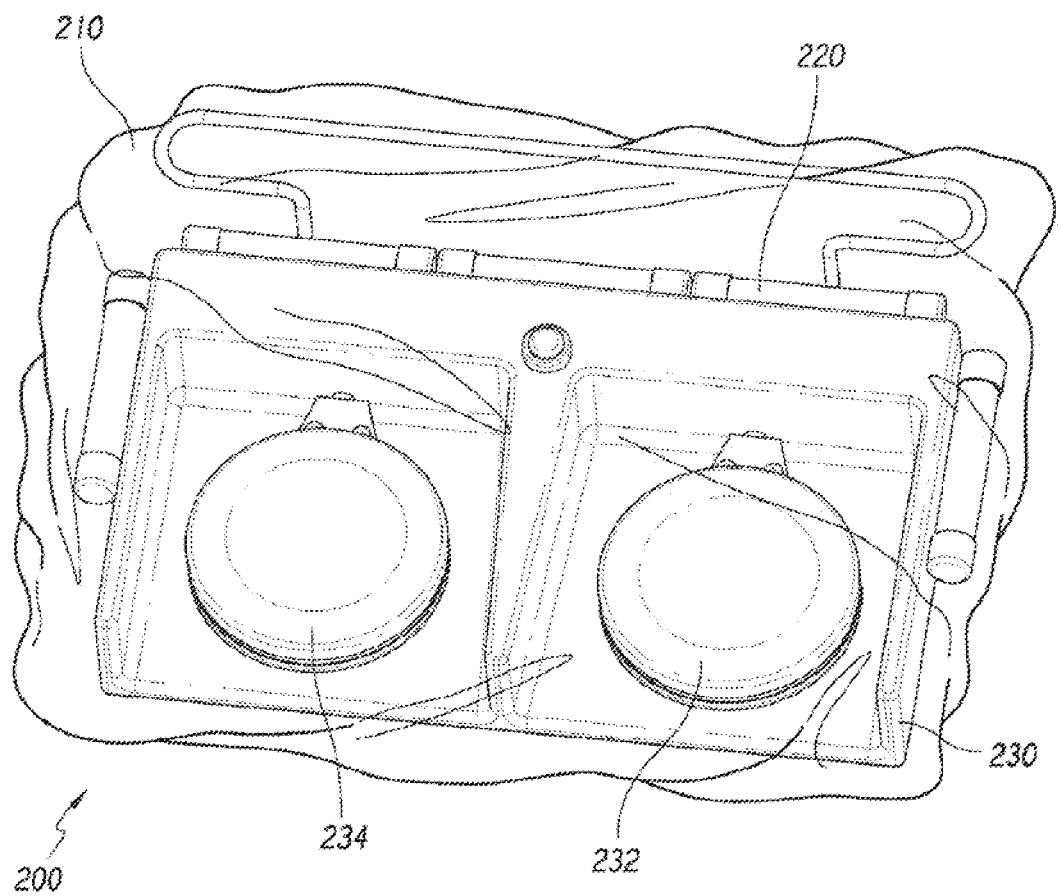
FIGS. 2A-2B illustrate an embodiment of an illuminated protective covering for a foot-activated device with two foot pedals.
Figure 2B:
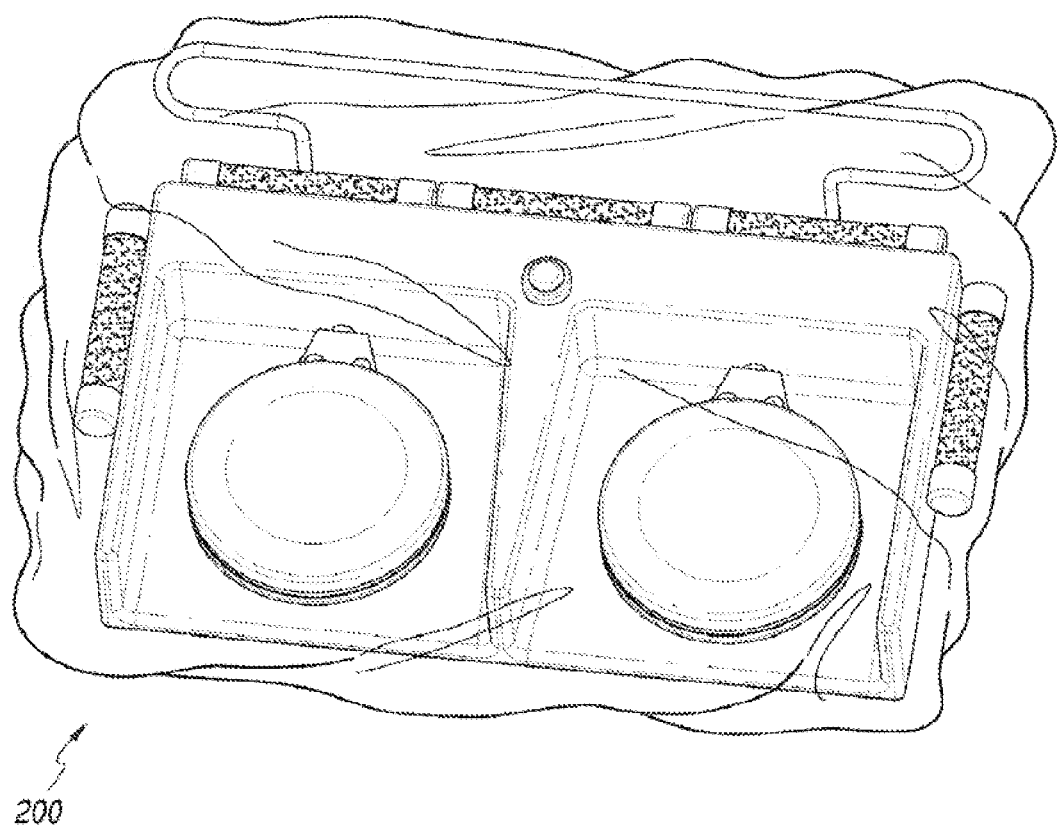
Figure 3A:
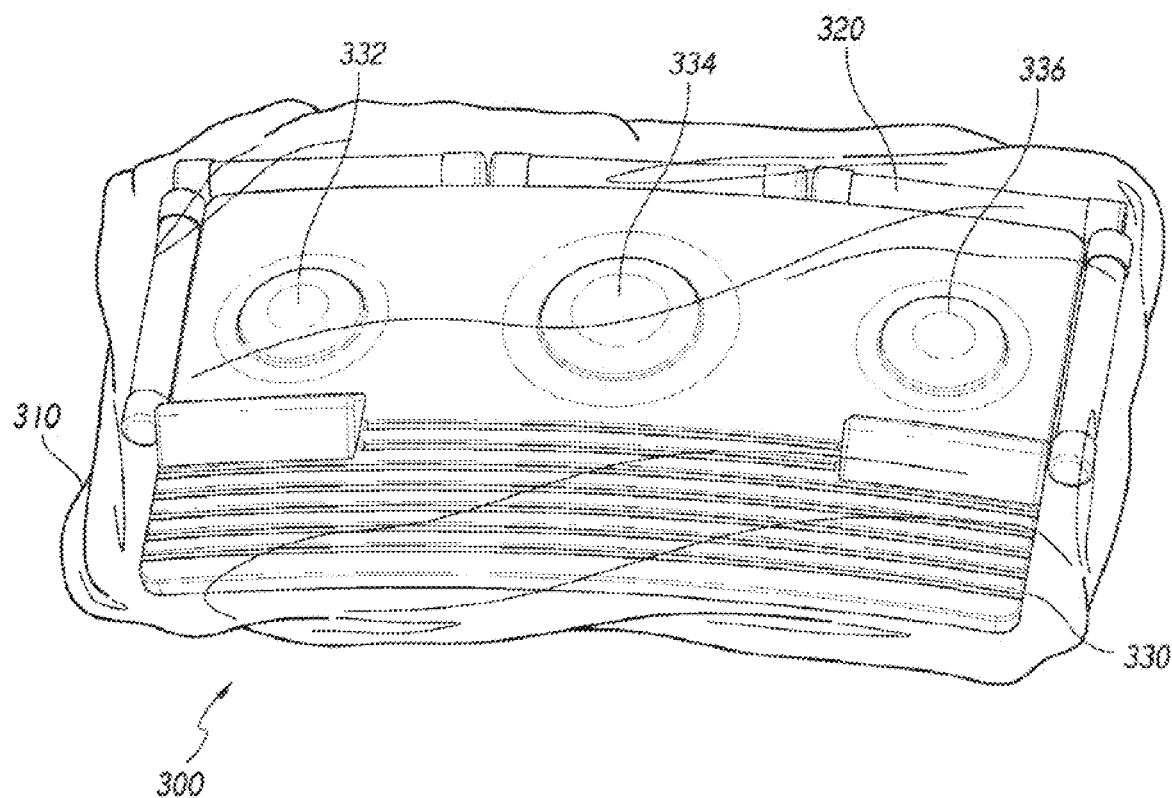
FIGS. 3A-3B illustrate an embodiment of an illuminated protective covering for a foot-activated device with three foot pedals.
Figure 3B:
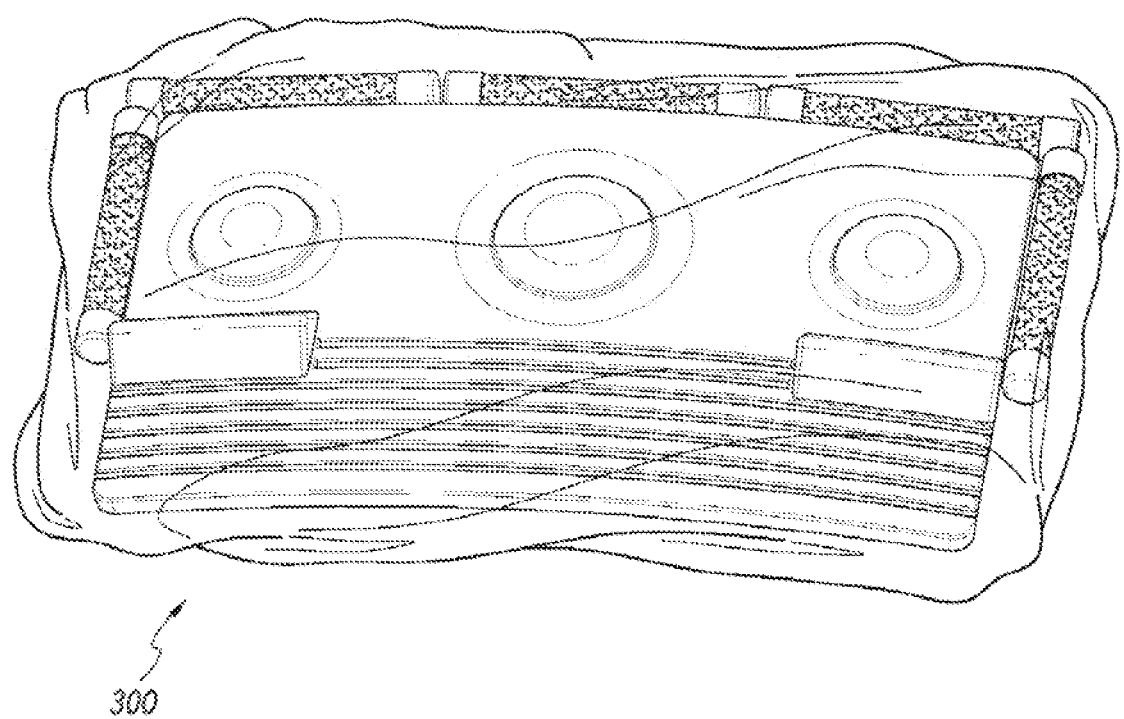

FIGS. 1A-1F, 2A-2B, 3A-3B, and 4A-4B illustrate embodiments of the illuminated protective cover covering various examples of foot pedals. As will be described in more detail below, the illuminated protective cover may include a protective sheet and a plurality of illuminating devices. The protective sheet may be transparent or translucent such that the illuminating device can brighten the foot pedal such that the user can visibly see the location of the foot pedal through the protective sheet in some examples, or may be fully or partially opaque in other examples. As seen in FIGS. 1B, 2B, and 3B, the brightness of the illuminating device allows the location of the foot pedal to be visible even in dim lighting. As seen in FIGS. 1D and 1F, the brightness of the fluorescence from the illuminated protective cover allows the location of the foot pedal to be visible even in dim lighting.

FIG. 1A illustrates an illuminated protective cover 100 disposed about a device 130 with a first pedal 132. In an embodiment, device 130 may be an example of a surgical device. As noted above, the illuminated protective cover 100 may include a protective sheet 110 and a plurality of illuminating devices 120 placed around the foot pedal 132 of the surgical device 130.

The protective sheet 110 may be in the form of a flat sheet or a bag. As described above, in some configurations, the protective sheet 110 may be customized for specific foot pedal designs. In other configurations, the protective sheet 110 may be sufficiently large to fit any sized device 130 and may be configured to allow a user to resize the protective sheet 110 as appropriate. For example, the protective sheet 110 may have a size of 20 inches by 20 inches. The protective sheet 110 may be wrapped or secured about the device 130 such that the protective sheet 110 folds or conforms to the surface of the foot pedal 132 of the device 130. The protective sheet 110 may provide a protective covering about the surgical device 130 but does not interfere with the function of the foot pedal 132 of the device 130.

The protective sheet 110 may be secured about the surface of the device 130 to protect the device 130 from moisture and other debris generated from the environment; for example, during the surgical procedure. For example, the protective sheet 110 may be secured by tying and/or knotting the ends of the protective sheet 110 about the device 130. Additionally or alternatively, the protective sheet 110 may be secured using adhesive, string, a wire, an elastic band, etc.

The protective sheet 110 may be made from or coated in an optically brightened material. For example, fluorescent compounds may be added to the protective sheet 110 to enhance the fluorescence of the material, or the protective sheet 110 may be manufactured having one or more fluorescent compounds in or on the material. These fluorescent compounds may be brightening agents added to or incorporated in the protective sheet 110 that emit visible light when illuminated with UV radiation. In some examples, the protective sheet 110 may be a white material or fabric formed with brightening agents so as to fluoresce responsive to activation of a UV illuminating device 120. In other examples, the protective sheet 110 may be formed in one or more other fluorescent colors so as to glow in various colors or patterns, including words or symbols, as will be readily understood by one of ordinary skill in the art. These varying colors and patterns may allow for identification of different foot pedals 132 having different functionalities.

In some examples, the protective sheet 110 may be made from a transparent or translucent material that allows the device 130 and the foot pedal 132 to be visible. The protective sheet 110 may be made of plastic. In other examples, the protective sheet 110 may be made from an opaque or partially opaque fabric or material, as will be readily understood by one having ordinary skill in the art. As well, the protective sheet 110 may be disposable and easily discarded after each use. A disposable protective sheet 110 may allow the disposable protective sheet 110 to be cheaply purchased by the user. As well, the disposable and customizable configuration of the protective sheet 110 also may reduce costs as the same disposable protective sheet 110 may be adapted to a device, such as a surgical instrument, of any shape or size.

The illuminated protective cover 100 may include one or more illuminating devices 120 that light up the device 130 and location of the foot pedal 132. In some examples the illuminating devices 120 may emit visible light that illuminates the device 130 and foot pedal 132 (see, e.g., FIGS. 1A-1B). In other examples, the illuminating devices 120 may emit UV light that causes the protective sheet 110 to fluoresce and thereby illuminate the device 130 and foot pedal 132 (see, e.g., FIGS. 1C-1F). The illuminating device 120 may be attached to at least one side adjacent to the foot pedal 132 of the device 130 in some embodiments (see, e.g., FIGS. 1A-1D, 2A-2B, 3A-3B, 4A-4C, 8A-8B). In other examples, the illuminating devices 120 may be attached to a frame surrounding the foot pedal 132 (see, e.g., FIGS. 5A-5L, 9A-9B), or may be positioned adjacent to but detached from the foot pedal 132 or frame (see, e.g., FIGS. 1E-1F, 5M, 8C-8D, 9C-9D). The illuminating devices 120 may be positioned inside or outside of the protective sheet 110, according to various embodiments. As illustrated in FIG. 1A, each of the plurality of surgical devices 130 may be attached such that an illuminating device 120 is placed on the surface of one end of the device 130, on the left of the device 130, and on the right of the device 130. This can allow the user to locate the position of the foot pedal 132 based on the illuminating device 120. In another embodiment, as illustrated in FIGS. 1E-1F, the illuminating devices 120 may be attached to an exterior surface of the protective sheet 110 at one or more positions about a periphery of the foot pedal 132. Various numbers of illuminating devices 120 and various positions of the illuminating devices 120 with respect to the foot pedal 132 are envisioned, as will be readily understood by one having ordinary skill in the art.

The height of the placement of each of the illuminating devices 120 also may be varied to allow the user to locate the foot pedal 132 and better adjust the position of the user's foot. The illuminating devices 120 may be placed at a number of heights such as the base of the device 130, between the base and the top surface of the device 130, or above the top surface of the device 130.

The plurality of illuminating devices 120 may be removably or permanently secured in a number of ways. In some examples, the plurality of illuminating devices 120 may be attached directly to the device 130. In some embodiments, the plurality of illuminating devices 120 may be secured to the inside or outside surface of the protective sheet 110. In other embodiments, one or more of the plurality of illuminating devices 120 may be secured to an object separate from the device 130, such as a table or stand, or other object as will be readily understood by one having ordinary skill in the art.

The plurality of illuminating devices 120 may be secured in a number of ways such as through using an adhesive or attaching each of the illuminating devices 120 with a separate component (e.g., a magnet, a clip, a wire, or otherwise) that may be configured to engage with the device 130 or the protective sheet 110. In other examples, the protective sheet 110 may include one or more pockets or other features to retain the illuminating devices 120.

The illuminating devices 120 may come in a variety of shapes and sizes. In some embodiments, the illuminating device 120 is tubular, while in other embodiments the illuminating device 120 may take the shape of any light bulb or other illuminating device as will be readily understood by one of ordinary skill in the art. The illuminating devices 120 may be rigid and any length. For example, the illuminating devices 120 may be attached end-to-end such that the illuminating devices 120 span the entire length of a side of the device or only a portion (e.g., substantially the entire length of a side of the device 130, a majority of the entire length of a side of the device 130, about half of the entire length of a side of the device 130, less than half of the entire length of a side of the device 130, or intermittently along the side of the device 130). The illuminating device 120 also may be bendable and/or malleable. For example, a single illuminating device 120 may be bent to wrap around portions of the device 130 (see, e.g., FIGS. 5E-5F).

The illuminating device 120 may be disposable so as to provide a one-time activation. For example, the structure may make light through chemiluminescence, with the outer covering being rigid or flexible. In some examples, the illuminating device 120 is a glow stick. A disposable illuminating device 120 may allow the disposable illuminating device 120 to be cheaply purchased by the user. As well, the disposable and customizable nature of the plurality of disposable illuminating devices 120 also may reduce costs as the same disposable illuminating devices 120 may be attached to a surgical device of any shape or size.

The illuminating device 120 also may be non-disposable. For example, each illuminating device 120 may be composed of one or more LEDs in some examples, or fluorescent blacklight tubes emitting UV light in other examples. In some examples, the illuminating device 120 may be a blacklight blue (BLB) UV tube, having a dark blue filter coating so as to filter out most visible light. The illuminating device 120 may be battery powered or require an electrical outlet to provide power. The illuminating device 120 may include an on and off switch to activate the illuminating device 120.

In some examples, the illuminating device 120 may be configured to emit a red light. Red lights have lower wavelengths and may be less disruptive to the eye in a darkened environment. In other examples, the illuminating device 120 may come in any variety of colors such as red, blue, green, yellow, purple, orange, pink, etc. When a plurality of devices or foot pedals are being used, the multiple colors of illuminating devices 120 may be used to help the user identify the purpose of each of the illuminating devices 120.

FIGS. 2A and 3A illustrate illuminated protective covers 200, 300 disposed about devices 230, 330 that include a plurality of foot pedals. In an embodiment, devices 230, 330 may be examples of surgical devices. The illuminated protective covers 200, 300 resemble or are identical to the system 100 in many respects. Accordingly, numerals used to identify components of the illuminated protective covers 200, 300 are incremented by a factor of one hundred to identify like features of the illuminated protective covers 200, 300. This numbering convention generally applies to the remainder of the figures. Any component or step disclosed in any embodiment in this specification may be used in other embodiments.

The illuminated protective cover 200, like the illuminated protective cover 100, includes a protective sheet 210 and a plurality of illuminating devices 220. The illuminated protective cover 200 is disposed about the device 230 that includes a foot pedal 232 and a foot pedal 234. Each of a plurality of illuminating devices 220 is attached around the device 230 to frame the borders of the device 230. As shown in FIG. 2B, the placement of the plurality of illuminating devices 220 may allow the user to see the location of the foot pedal 232 and foot pedal 234 on the surgical device 230.

The placement of the illuminating device 220 also may provide the user with a frame of reference of where the foot should be placed to engage either of the foot pedals. For example, the user may use the location of the plurality of illuminating devices 220 to know that by placing his foot closer to the right-most illuminating device 220, he will activate the foot pedal 232 located on the right. Similarly, the user will know that by placing his foot closer to the left-most illuminating device 220, he will activate the foot pedal 234 located on the left. The illuminating devices 220 also may be placed between each of the foot pedals 232, 234 such that the user can easily identify the location of each of the foot pedals 232, 234.

Similarly, FIG. 3A illustrates an example of how the illuminated protective cover 300 may allow the user to identify and easily locate a surgical device 330 with a plurality of pedals. The illuminated protective cover 300 includes a protective sheet 310 and a plurality of illuminating devices 320 disposed about the surgical device 330. Because of the number of foot pedals on the device 330, the device 330 is wider than the devices illustrated in FIGS. 1A and 2A. To frame the device 330, the illuminated protective cover 300 may include additional illuminating devices 320 to frame/line the front end of the device 330. In some examples, a plurality of illuminating devices 320 may be attached to the device 330 such that the plurality of illuminating devices 320 line up end-to-end. In the device 330 illustrated in FIG. 3A, the device 330 includes a foot pedal 332, a foot pedal 334, and a foot pedal 336.

As with FIG. 2B, FIG. 3B illustrates the illuminated protective cover 300 illuminating the device 330 in a darkened environment. In some examples, because of the placement of the plurality of illuminating devices 320, the user will be able to locate the foot pedal 332 near the left-most illuminating device 320, the foot pedal 336 near the right-most illuminating device 320, and the foot pedal 334 by placing his foot in the middle of the device 330 framed by the plurality of illuminating devices 320. The illuminating devices 320 also may be placed between each of the foot pedals 332, 334, 336 such that the user can easily identify the location of each of the foot pedals 332, 334, 336.

The illuminated protective cover may be configured to accommodate a surgical device with any number of foot pedals. By using the plurality of illuminating devices to frame the outside surface of the device, the illuminating devices may allow the user to see the foot pedals, or to provide the user with a frame of reference as to where he is placing his foot. As well, as described above, an illuminating device may be placed between each of the foot pedals to help the user more precisely locate each of the foot pedals on the device.

Figure 4A:
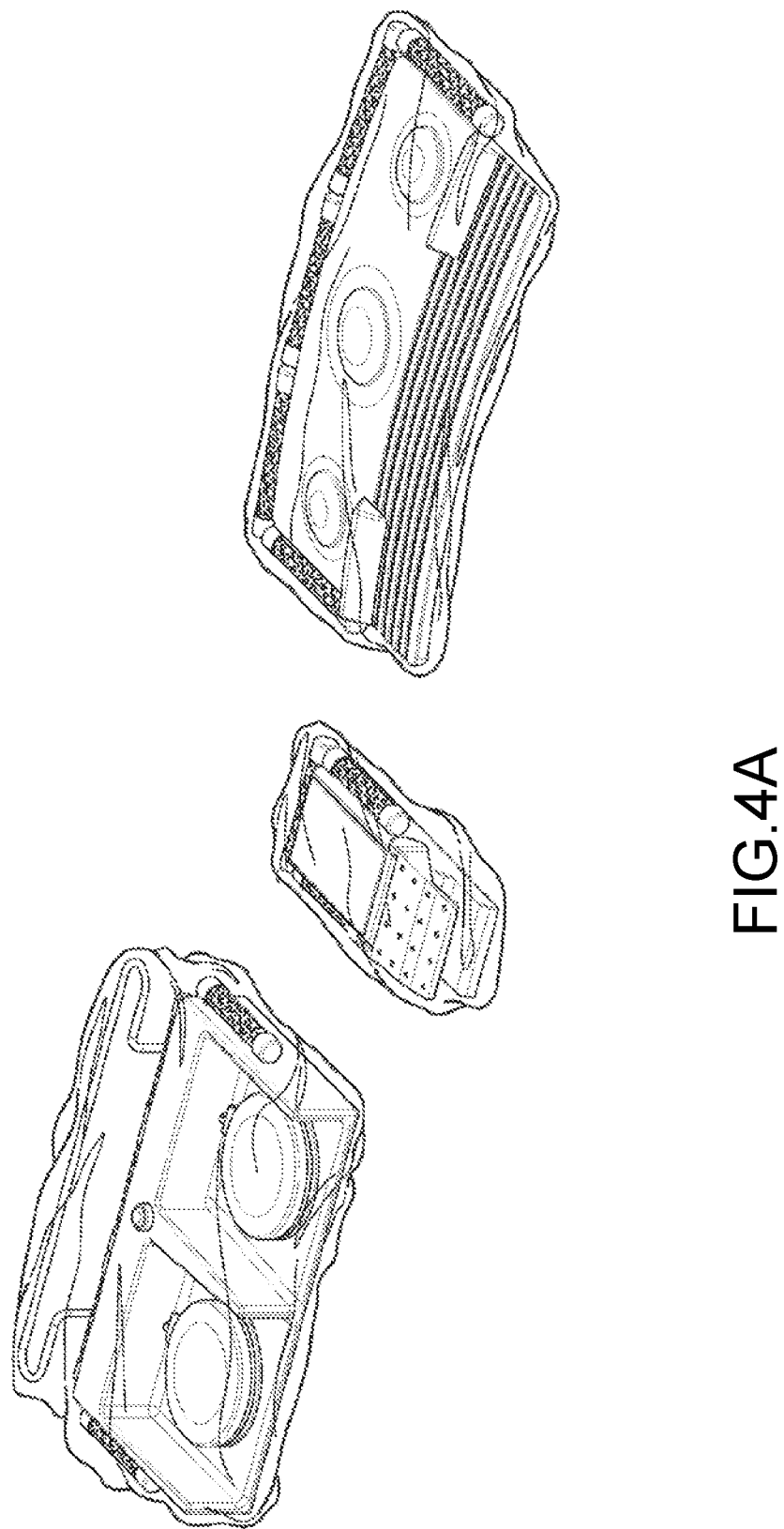
FIGS. 4A-4C illustrate the illuminated protective coverings of FIGS. 1A-1F, 2A-2B, and 3A-3B activated in a darkened environment.
Figure 4B:
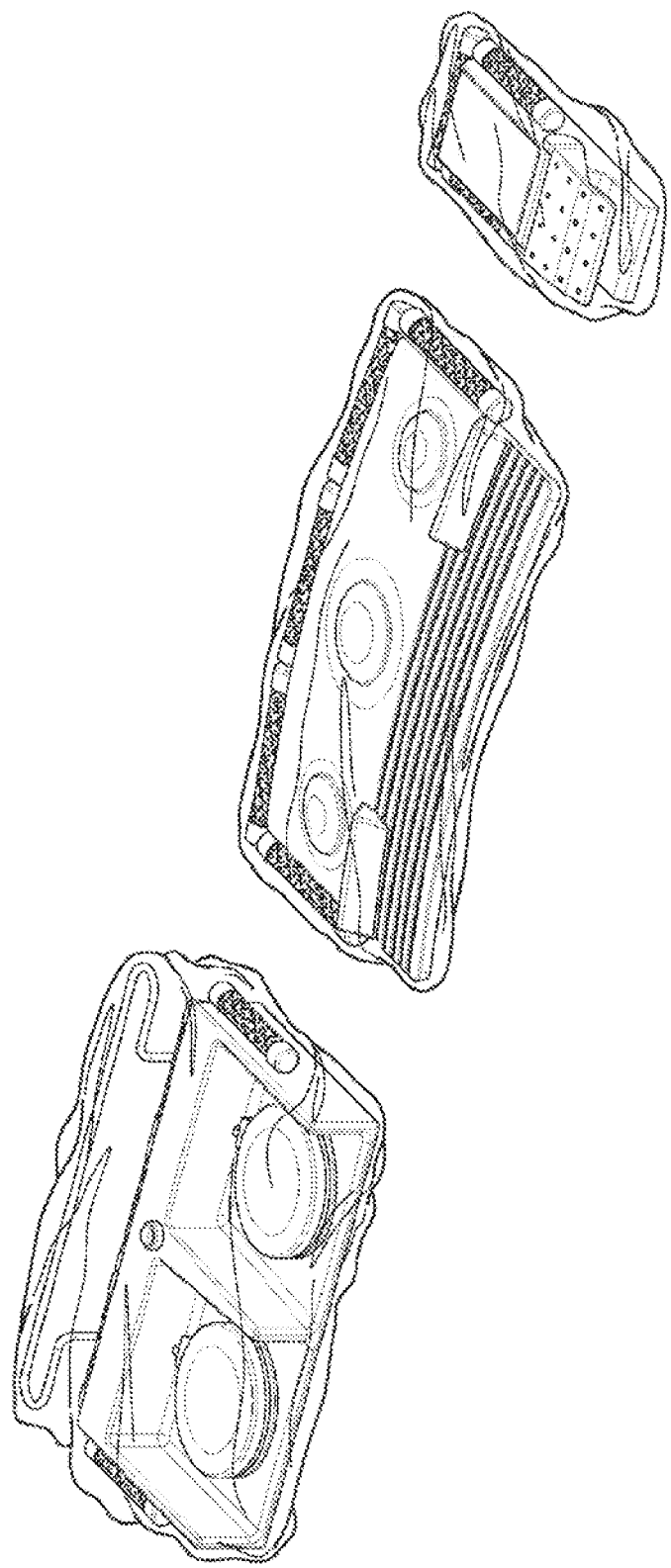
Figure 4C:
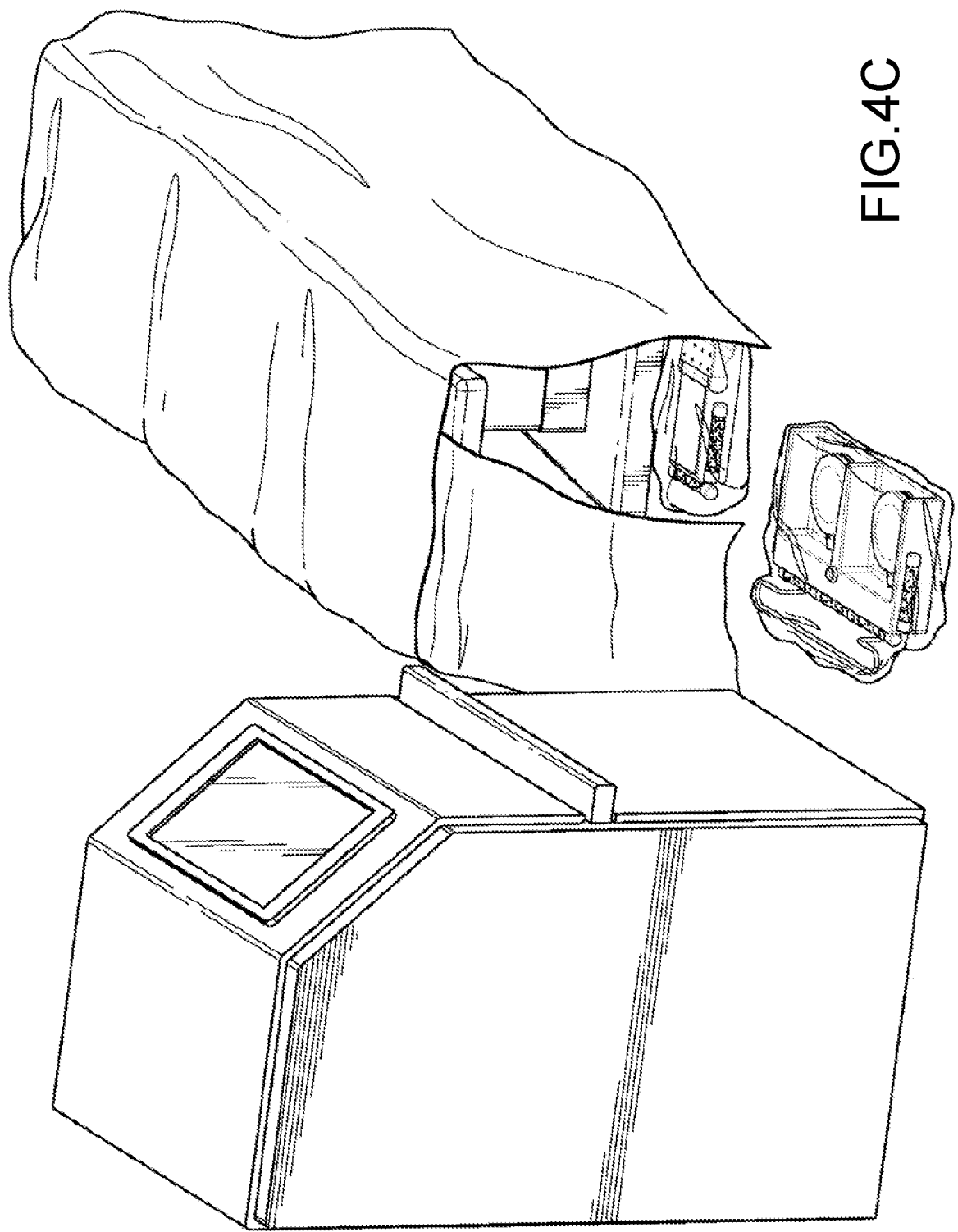

FIGS. 4A-4C illustrate various embodiments of illuminated protective covers on a variety of different-sized devices. As seen, the illuminated protective covers allow each of the devices and their associated foot pedals to be easily identified in a darkened operating room.

Optically Brightened Coating and Illuminating Device(s)

FIGS. 8A-8D and 9A-9D illustrate embodiments of the illuminated cover in which the illuminated cover includes an optically brightened coating. The optically brightened coating may be applied to the foot pedal and/or a frame surrounding the foot pedal such that, when an ultraviolet illuminating device is directed toward the foot pedal and/or frame, the optically brightened coating fluoresces, thereby brightening the foot pedal and/or frame such that the user can visibly see the location of the foot pedal. As seen in FIGS. 8B, 8D, 9B, and 9D, the brightness of the fluorescence of the optically brightened coating induced by the ultraviolet illumination from the illuminating device allows the location of the foot pedal to be visible even in dim lighting.

Figure 8B:
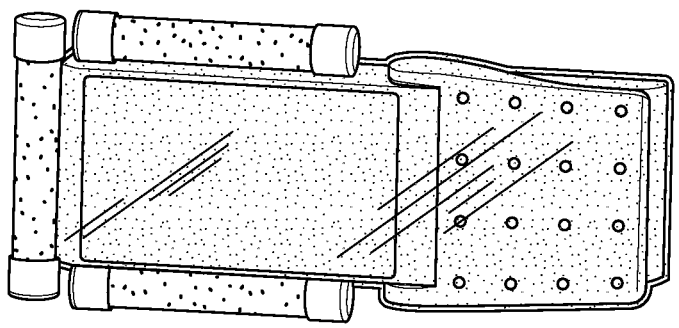
FIGS. 8A-8D illustrate an embodiment of an optically brightened coating for a foot-activated device with a single foot pedal.
Figure 8A:
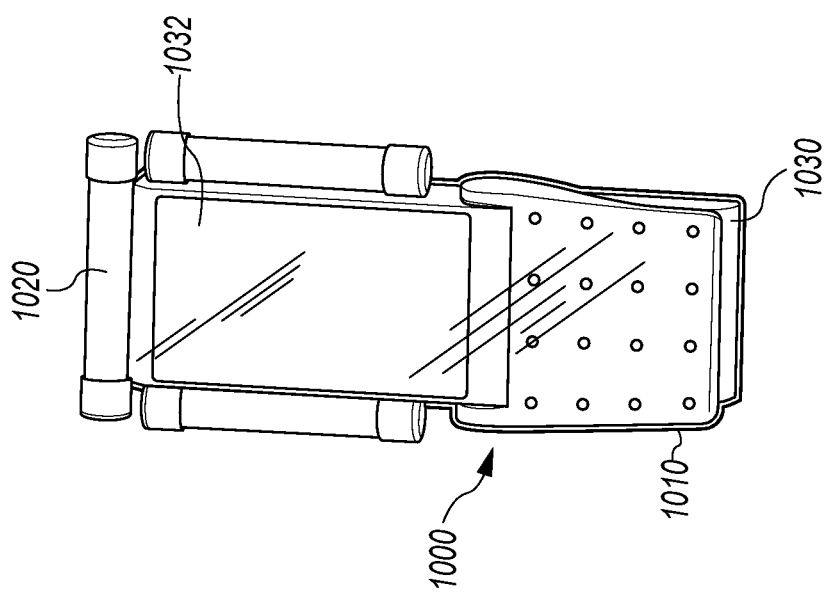
Figure 8D:
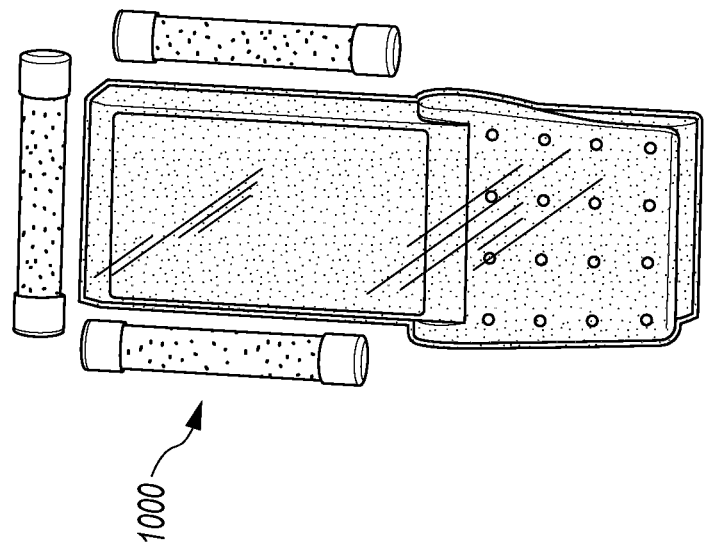
Figure 8C:
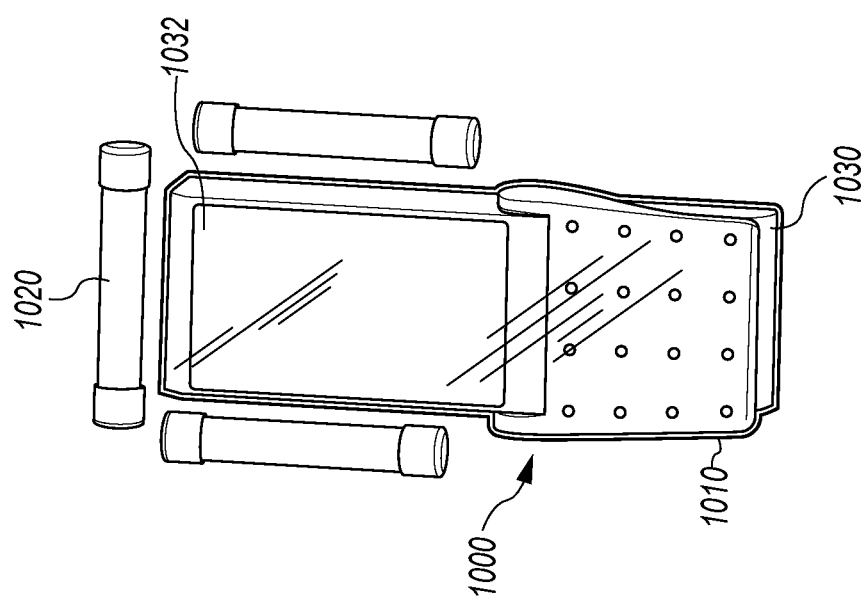
Figure 9A:
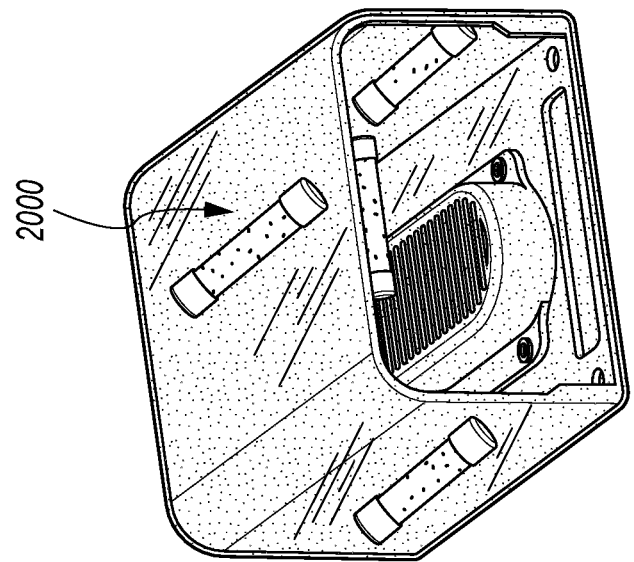
FIGS. 9A-9D illustrate an embodiment of a protective frame that may be used with an optically brightened coating, wherein the protective frame is disposed about a foot-activated device and the illuminating device may be located in a number of different locations.
Figure 9B:
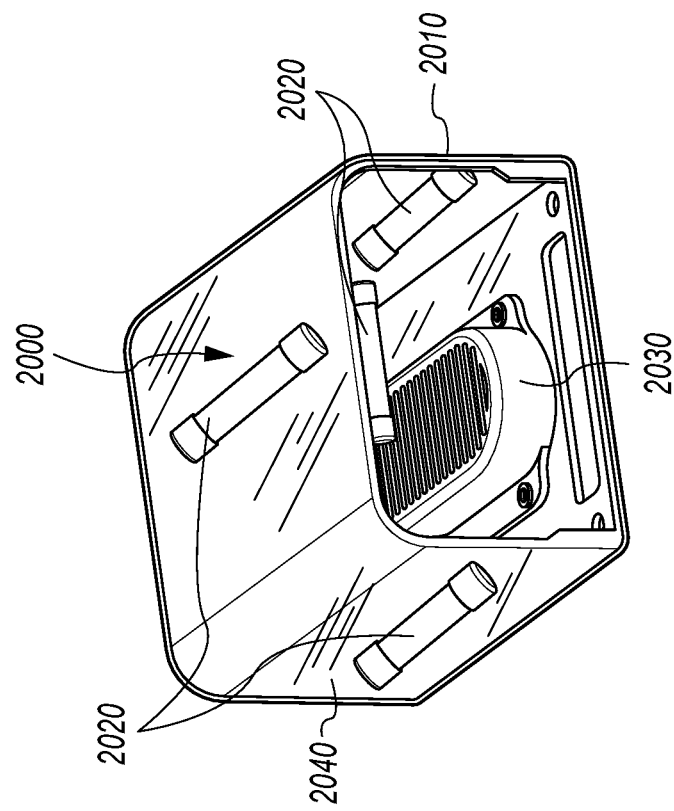
Figure 9D:
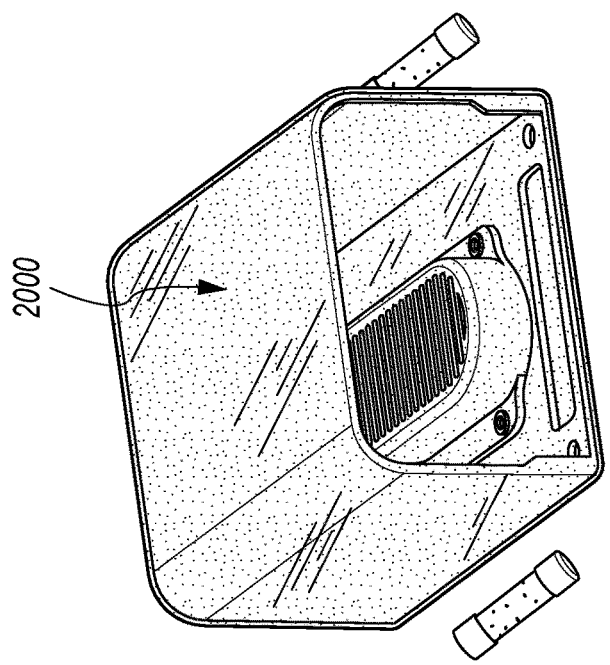
Figure 9C:
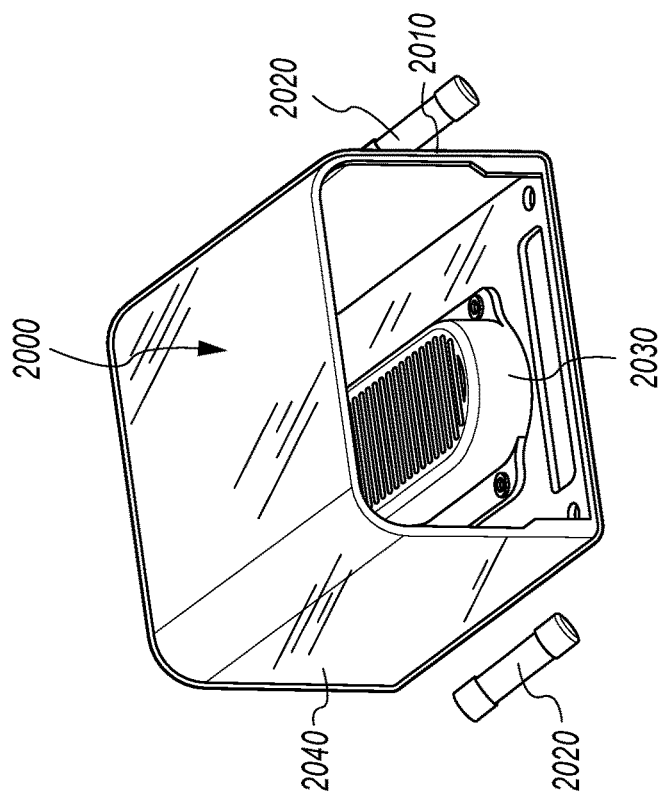

FIGS. 8A and 8C illustrate an illuminated cover 1000 disposed about a device 1030 with a first pedal 1032. In an embodiment, device 1030 may be an example of a surgical device. As noted above, the illuminated cover 1000 may include an optically brightened coating 1010 and a plurality of illuminating devices 1020 placed around the foot pedal 1032 of the surgical device 1030. In some embodiments, for example as illustrated in FIG. 8A, the plurality of illuminating devices 1020 may be attached to the device 1030, while in other embodiments, for example as illustrated in FIG. 8C, the plurality of illuminating devices 1020 may be detached from the device 1030 and positioned somewhere in proximity to the device 1030 so as to emit t onto the illuminated cover 1000 of device 1030 and cause the illuminated cover 1000 to fluoresce. Although illustrated in FIG. 8C as being positioned at the same elevation as the foot pedal 1032, ire other embodiments the plurality of illuminating devices 1020 may be positioned above the device 1030 at various heights, distances, and angles, as will be readily understood by one of ordinary skill in the art.

The optically brightened coating 1010 may be applied to at least a portion of the foot pedal 1032. For example, the optically brightened coating 1010 may cover at least a part or all of an upper surface of the foot pedal 1032. In some examples, the optically brightened coating 1010 may be applied to the surgical device 1030 in the nature of a spray or liquid paint, for example. The spray or liquid paint may include an optical brightening agent that absorbs ultraviolet light and emits visible light as fluorescence. In other examples, the surgical device 1030 may be formed from a material having an optical brightening agent incorporated therein. The optically brightened coating 1010 may provide a full or partial coating of the surgical device 1030 but does not interfere with the function of the foot pedal 1032 of the device 1030.

As shown in FIGS. 8A and 8B, the one or more illuminating devices 1020 may be positioned to attach to one or more top or side portion of the surgical device 1030 in some examples. In other examples, as illustrated in FIGS. 8C and 8D, the one or more illuminating devices 1020 may be positioned adjacent to the surgical device 1030. In any embodiment, the one or more illuminating devices 1020 may be positioned to emit ultraviolet light toward the surgical device 1030. The optically brightened coating 1010 may absorb the emitted ultraviolet light and fluoresce so as to made the surgical device 1030 visible to users in low ambient light.

Frame

In some examples, the illuminated protective cover further or alternatively may include a frame. The device may be placed within the frame such that the device may be provided with additional protection, for example during a surgical procedure. The frame also may provide sufficient weight to prevent the device and frame from moving during use of the device. In other examples, the frame may provide an additional surface for the attachment of the plurality of illuminating devices. In some examples, the frame may give the device added height such that the top surface of the foot pedal is better illuminated. In some embodiments, the frame may contain the illumination such that the environment around the foot pedal is brightened.

Each of the frames 440, 940, 2040 disclosed below may be configured to be part of the device or a separate component. The frames 440, 940, 2040 may be reusable or a disposable component that may be discarded after each use. In some examples, the frame may be made of an inexpensive plastic material.

FIGS. 5A-5M illustrate an example of a frame 440. As shown in FIGS. 5A-5M, the frame may include one or more walls, e.g., a top wall, a bottom wall, a left wall, a right wall, and/or a back wall. In some examples, the five (5) walls of the frame 440 form a closed container. In some examples, the top wall, the bottom wall, the left wall, and the right wall form an opening of the frame 440. The frame 440 can provide the illuminated protective cover with additional surfaces to place the illuminating device to better visualize the foot pedal of the device.

Figure 5D:
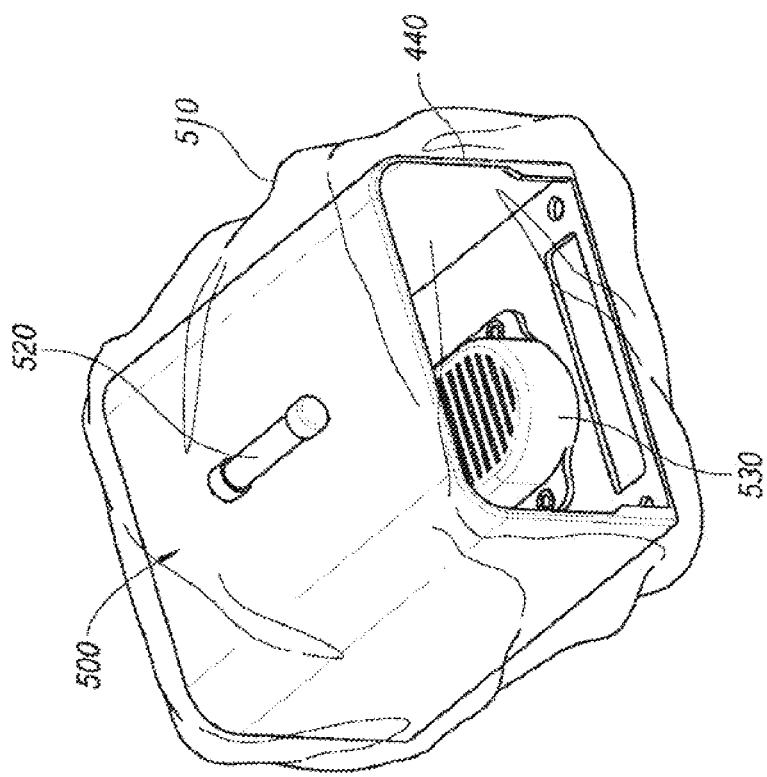
Figure 5C:
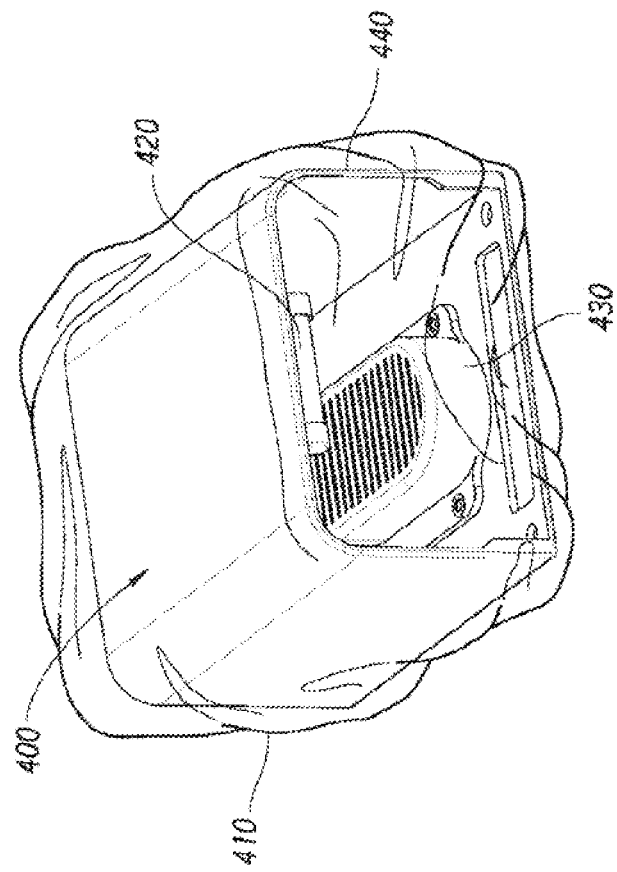

FIGS. 5A-5C illustrate an example of the illuminated protective cover 400 with the frame 440. As illustrated, the frame 440 includes a device 430 placed within the frame 440 such that the device 430 is attached adjacent to the inside bottom surface of the frame 440. The protective sheet 410 of the illuminated protective cover 400 is wrapped around the entirety of the illuminated protective cover 400 to cover the exterior and interior surfaces of the frame 440. As well, the protective sheet 410 seals the device 430 while allowing access to the device 430 by the user by placing his foot through the opening of the frame 440. Though illustrated in FIGS. 5A-5C as a protective sheet 410, in other examples the illuminated cover may include an optically brightened coating applied to the exterior and/or interior of the frame 2040, for example as illustrated in FIGS. 9A-9D.

In the example illustrated in FIGS. 5A-5C, the illuminating device 420 is placed on the interior surface of the top wall of the frame 440. The location of the illuminating device 420 allows for the entirety of the interior of the frame 440 to brighten. In FIGS. 5A-5C, the location of the illuminating device 420 allows the user to identify the foot pedal of the device 430 within the frame 440 while the top surface of the frame 440 prevents the illuminating device 420 from being disruptive to the user in the darkened environment.

FIG. 5D illustrates an example of the illuminated protective cover 500 with the frame 440. The illuminated protective cover 500 resembles or is identical to the illuminated protective cover 400 in many respects. Accordingly, numerals used to identify components of the illuminated protective cover 400 are incremented by a factor of one hundred to identify like features of the system for illuminated protective cover 500. This numbering convention generally applies to the remainder of the figures. Any component or step disclosed in any embodiment in this specification may be used in other embodiments. The illuminating device 520 of the illuminated protective cover 500 is attached to the exterior surface of the top wall of the frame 440. The protective sheet 510 seals the device 530 while allowing access to the device 530 by the user by placing his foot through the opening of the frame 440. The location of the illuminating device 520 allows the user to identify the location of the device 530 placed within the frame 440. The height of the illuminating device 520 may allow the user to position his foot appropriately to access the interior of the frame 440. In some examples the illuminating device 520 is positioned such that the protective sheet 510 covers the illuminating device 520, while in other examples the illuminating device 520 may be positioned externally to the protective sheet 510 and may be attached to the outer surface of the protective sheet 510.

Figures 5E, 5F:
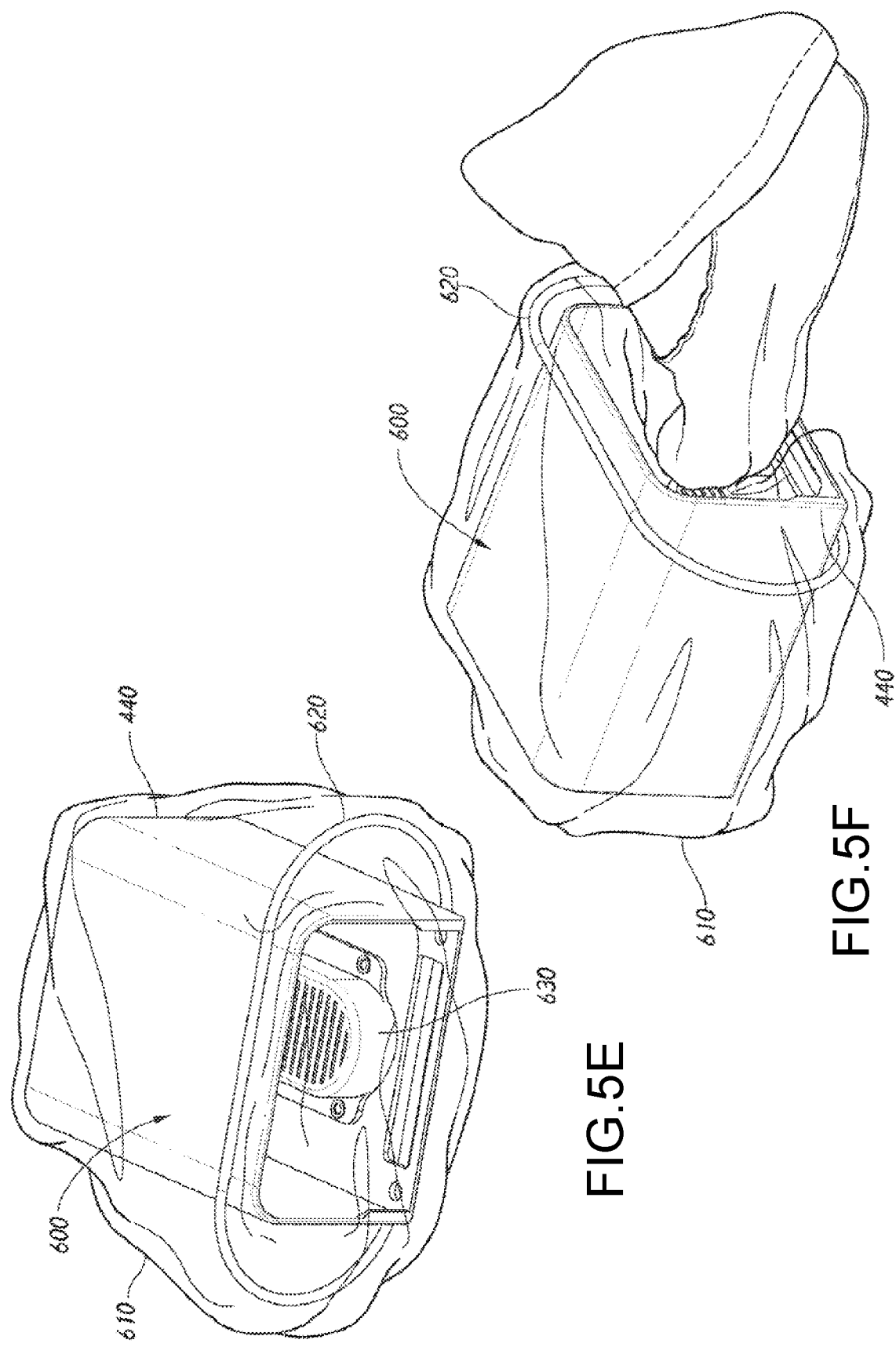

FIGS. 5E-5F illustrate the illuminated protective cover 600 with the frame 440. The illuminating device 620 of the illuminated protective cover 600 is located around the entirety of the opening of the frame 440. The protective sheet 610 seals the device 630 while allowing access to the device 630 by the user by placing his foot through the opening of the frame 440. The location of the illuminating device 620 allows the user to locate where his foot should be placed in order to access the device 630 located on the interior of the frame 440.

Figure 5H:
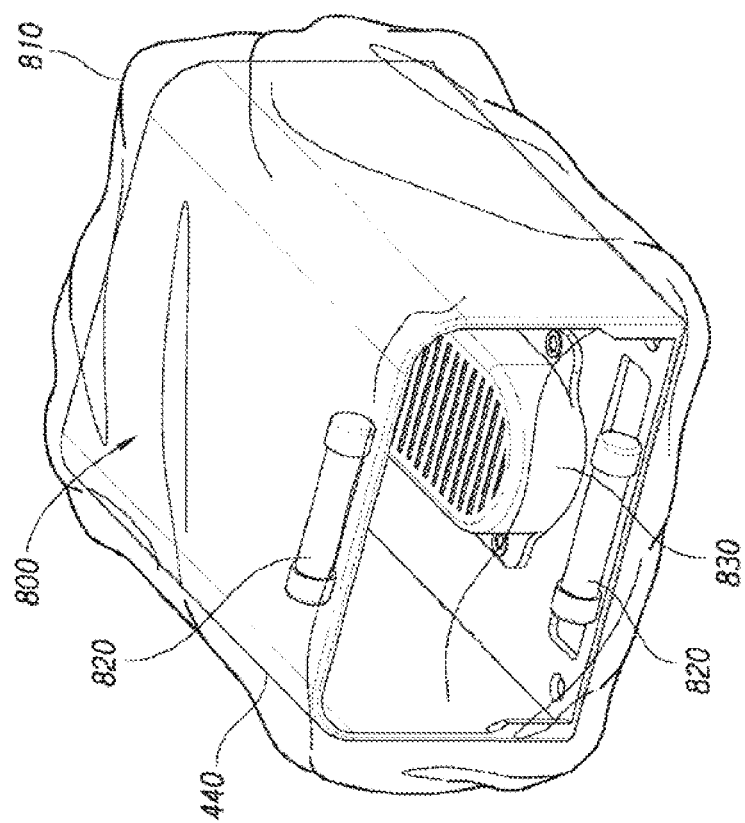
Figure 5G:
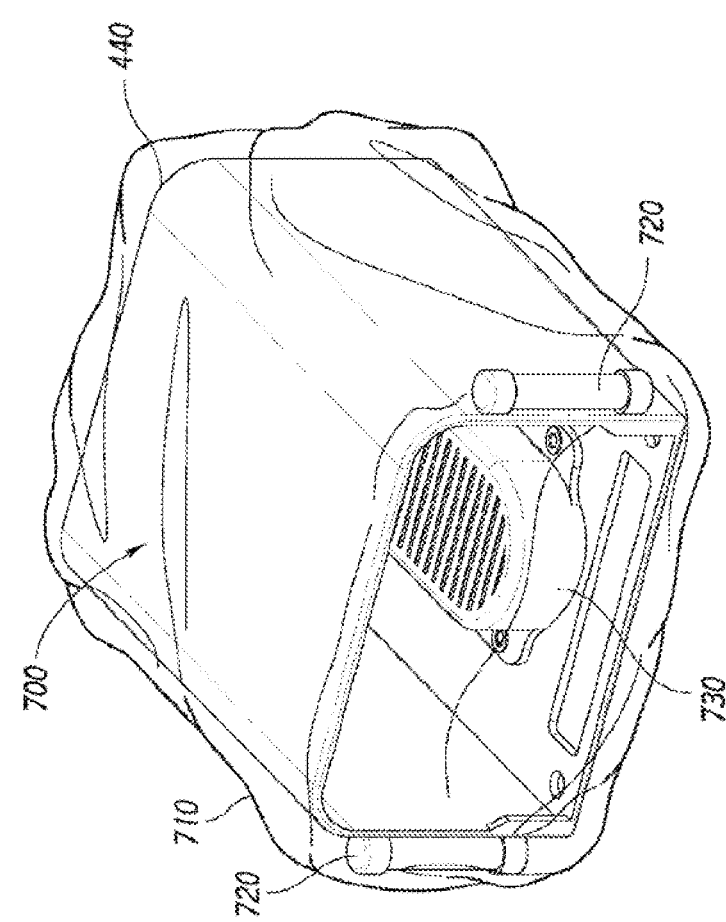
Figure 5J:
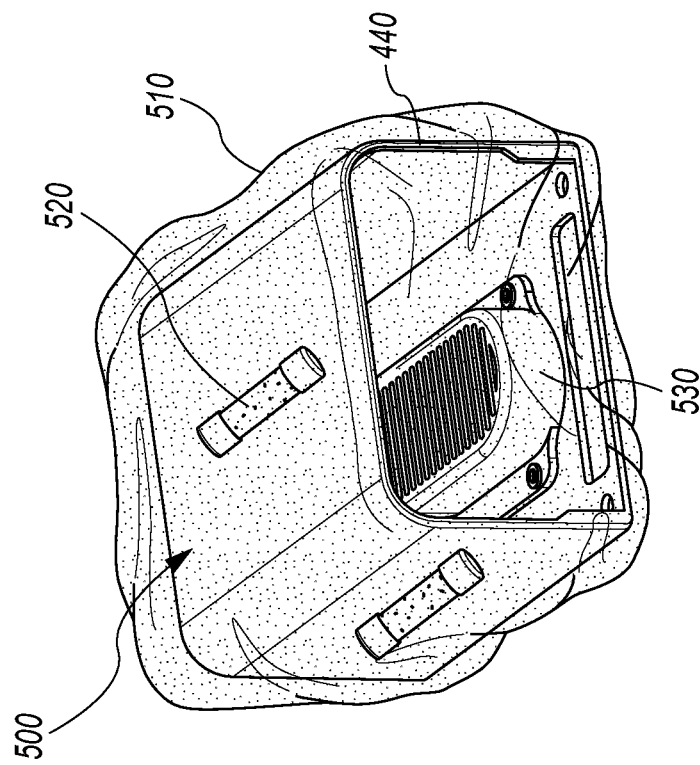
Figure 5I:
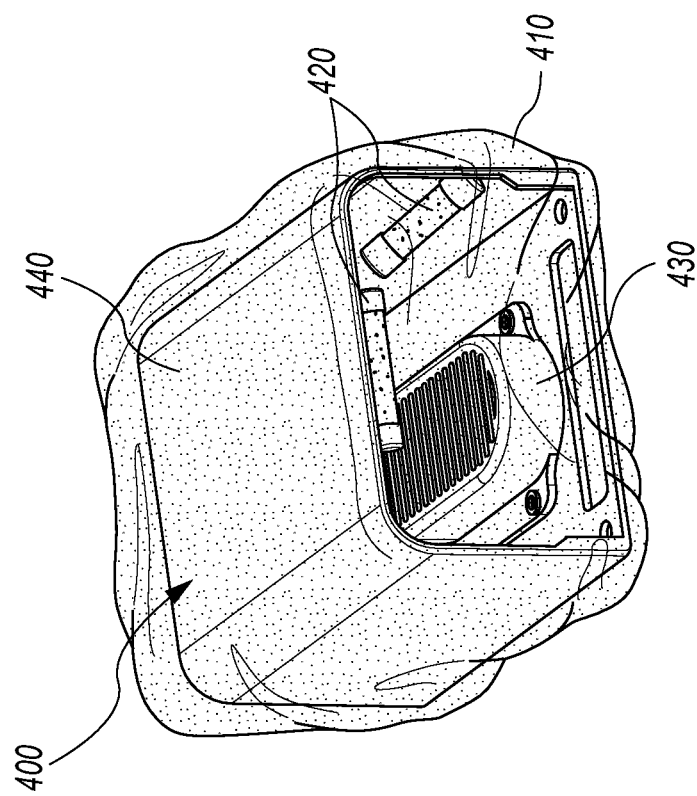
Figure 5K:
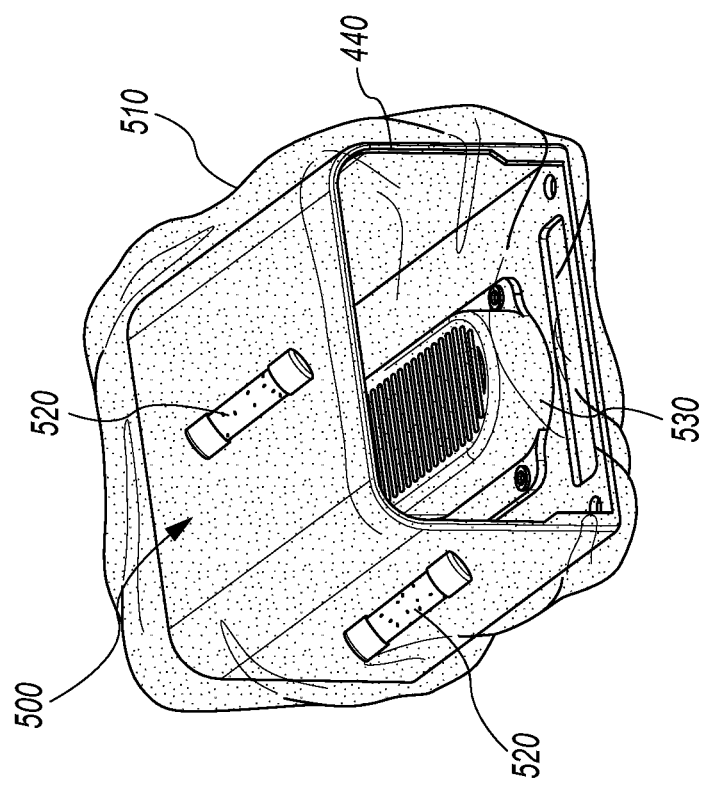
Figure 5L:
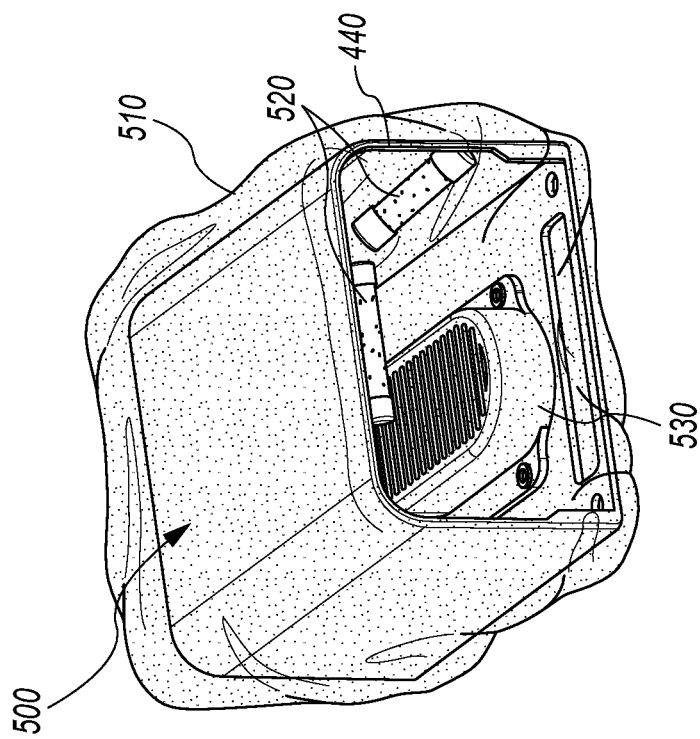
Figure 7:
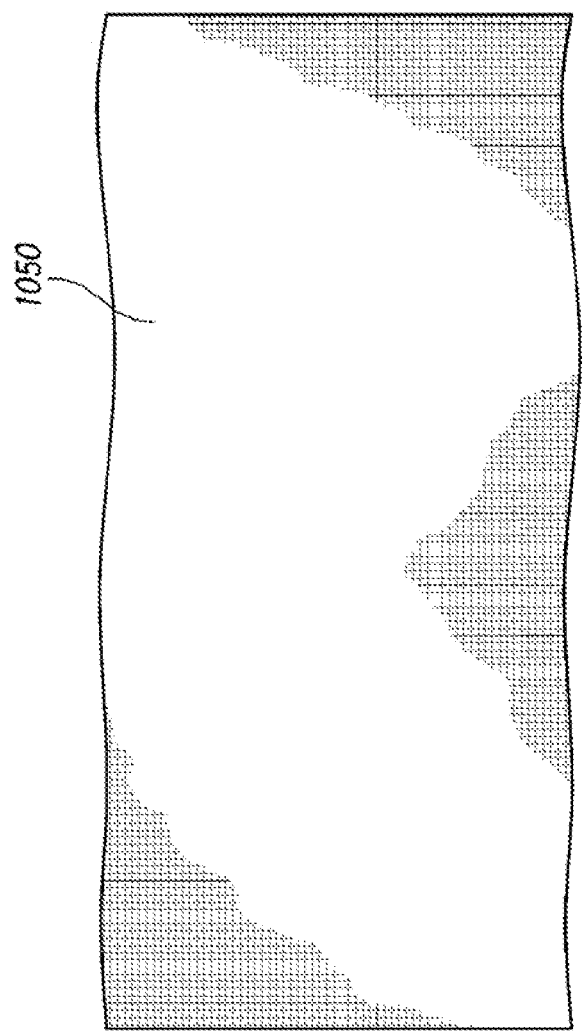
FIG. 7 illustrates an embodiment of an adhesive friction surface.

FIGS. 5G and 5H illustrate illuminated protective covers 700, 800 with a frame 440. In each of the illuminated protective cover 700 and the illuminated protective cover 800, a pair of illuminating devices 720, 820 is attached to opposing sides of the opening of the frame 440. In the illuminated protective cover 700, the pair of illuminating devices 720 is placed on the left and right sides of the opening of the frame 440. In the illuminated protective cover 800, the illuminating devices 820 are placed on the top and bottom ends of the opening of the frame 440. The protective sheet 710, 810 seals the device 730, 830 while allowing access to the device 730, 830 by the user by placing his foot through the opening of the frame 440. The location of the plurality of illuminating devices 720, 820 provide the user, for example a surgeon, with a reference point as to where the surgeon should place his foot in order to access the surgical device 730, 830 located within the frame 440.

FIGS. 5I-5M illustrate embodiments in which the illuminated protective covers 500 include an optically brightened layer, and in which the one or more illuminating devices 520 emit ultraviolet light that cause the illuminated protective covers 500 to fluoresce, thereby allowing for visualization of the surgical device 530 located within the frame 440. In various embodiments, the one or more illuminating devices 520 may be positioned in combinations of inside and outside the frame 440, inside and outside the illuminated protective covers 500, and attached to or detached from the frame 440. The various placements of the one or more illuminating devices 520 may allow for various portions of the illuminated protective covers 520 to fluoresce, such that a surgeon may visualize the position of the surgical device 530 and/or the frame 440.

FIGS. 9A-9D illustrate various embodiments in which external and/or internal surfaces of the frame 2040 are at least partially covered by an illuminated cover 2000 in the form of an optically brightened coating. In some embodiments, only the exterior of the frame 2040 may be partially or fully covered in the optically brightened coating, while in other embodiments, only the interior of the frame 2040 may be partially or fully covered in the optically brightened coating. In still other embodiments, a combination of the interior and exterior of the frame 2040 may be partially or fully covered in the optically brightened coating. In some embodiments, the frame 2040 may be formed from a material having inherent fluorescent components, or may be formed from a material with added optical brighteners. In other embodiments, the optically brightened coating may be applied to some or all of the interior and/or exterior of the frame 2040 in the form of a liquid or powder spray or paint, for example, or by other means known in the art. In some embodiments, the optically brightened coating may be applied to the frame 2040 to form one or more words, symbols, or patterns. In some embodiments, the optically brightened coating may be applied in one color or a combination of two or more colors so as to fluoresce in various colors for purposes of identifying the foot pedal used.

In various embodiments, the one or more illuminating devices may be positioned in any combination of inside the frame, outside the frame, attached to the frame, and/or detached from the frame. The one or more illuminating devices may provide illumination in the form of UV light that, when directed onto the surfaces that are partially or fully covered in the optically brightened coating, cause the optically brightened coating to fluoresce. This fluorescence may help a surgeon to visualize the positioning of the one or more foot pedals.

FIGS. 6A-6C illustrate another example of the frame 940. The frame 940 includes a bottom surface 942, a first wall 944, a second wall 946, and a third wall 948. The first wall 944 includes a top edge 944a and a bottom edge 944b. The second wall 946 includes a top edge 946a and a bottom edge 946b. The third wall 948 includes a top edge 948a and a bottom edge 948b. In some examples, a surgical device (e.g., a foot pedal) may be placed adjacent to the bottom surface 942 of the frame 940. Like the frame 440 illustrated in FIGS. 5A-5M, the protective cover for the illuminated protective cover may be placed around the frame 940 and the device. In other examples, where the illuminated cover is an optically brightened coating, the optically brightened coating may be applied to at least a portion of the interior and/or exterior surface of the frame 940 (see, e.g, FIGS. 9A-9D).

In some examples, the walls (e.g. the first wall 944, the second wall 946, and the third wall 948) of the frame 940 provide an elevated height for the placement of the plurality of illuminating devices 920. In some examples, the plurality of illuminating devices 920 may be secured to the exterior or interior surface of the walls of the frame 940. FIGS. 6A-6C illustrate three combinations of the placement of the illuminating devices 920, but the combinations are not intended to be limiting. The height of each of the plurality of illuminating devices 920 may be varied so as to better allow the illumination of the device to be placed within the frame 940. In some examples, the illuminating device 920 may be located near the bottom edge 944b, 946b, 948b of the interior or exterior surface of a wall (e.g., the first wall 944, the second wall 946, and the third wall 948) of the frame 940. In some examples, the illuminating device 920 may be located between the top edge 944a, 946a, 948a and bottom edge 944b, 946b, 948b of the interior or exterior surface of a wall (e.g., the first wall 944, the second wall 946, and the third wall 948) of the frame 940. The illuminating device 920 can also be located near the top edge 944a, 946a, 948a of the interior or exterior surface of a wall (e.g., the first wall 944, the second wall 946, and the third wall 948) of the frame 940.

As discussed above, in some examples, each of the illuminating devices 920 may be removably or permanently secured to the frame 940 using adhesive or a separate component (e.g., a wire, a clip, a magnet, or otherwise). In some examples, the frame 940 includes retention components (e.g., one or more projections to hold the illuminating device, an opening or pocket to receive the illuminating device, etc.) that extend from the exterior and/or the interior surface of the first wall 944, the second wall 946, and/or the third wall 948 to which the plurality of illuminating devices 920 may be secured.

Each of the frames 440, 940 disclosed above may be configured to accommodate a device of any size. In some examples, the frames 440, 940 may be adjustable. For example, the top wall, bottom wall, and back wall of the frame 440 may be configured such that the frame 440 may be widened or shortened to accommodate a wider or narrower device. In the same way, the frame 940 may include a bottom surface 942 and a third wall 948 that may be widened or shortened to accommodate a wider or narrower device. The adjustable walls may be constructed of two walls that are mechanically coupled such that they may be configured to slide against each other to lengthen or shorten.

Friction Surface

In some examples, the placement of the illuminated protective cover over the device may cause the bottom of the device to be slippery against the floor. To prevent slippage and/or movement of the device during use, a friction surface 1050 may be attached to (e.g., using an adhesive) or formed into or within a component of the illuminated protective cover. For example, the friction surface 1050 may be placed on the protective cover (e.g., frame or sheet) at the base of the device. The friction surface 1050 may include material properties and/or surface properties (e.g., adhesive properties, texturing) that prevent slippage when placed against the floor or other surface. The friction surface 1050 may reduce slippage such that the illuminated protective covered device remains stationary during use. In some embodiments, the friction surface 1050 may include an adhesive or a rubber surface that prevents slippage when placed against the floor or other surface. In some examples, the friction surface 1050 may be attached to the foot pedal device. In some embodiments, the protective cover may be attached directly to the floor. For example, the protective cover may be attached to the floor using an adhesive.

Methods of Use

Any of the illuminated protective covers described above may be attached to the device in a number of ways. The aforementioned illuminated devices may be attached to the pedal of the device using any of the attachment mechanisms described above. A protective cover then may be positioned over the device and secured in place.

The illuminated devices also may be attached directly to the protective cover. The protective cover, with the attached illuminated devices, then may be positioned over the device.

In some examples, the illuminated devices are first attached to a structure such as a frame. The device is placed within the frame and a protective cover is positioned over and secured about the frame.

In each of the aforementioned examples, the plurality of illuminated devices, the protective cover, and/or the frame may be removable between uses and/or between surgical procedures.

Alternative Configurations

In other embodiments, the illuminating devices may be secured separately from the foot pedal device, the frame, and/or the protective sheet. For example, FIGS. 5M, 8C, and 8D illustrate embodiments in which the illuminating devices are positioned adjacent to but secured separately from the foot pedal device. For example, an illuminating device may be placed under the patient's bed but above the foot pedal of the surgical device such that the illuminating device may illuminate the foot pedal. The illuminating device may be either disposable or reusable. For example, the illuminating device may include battery powered LED lights, chemiluminescent lights (e.g., glow lights, glow sticks) or other types of lights (e.g., fluorescent, CFL, halogen, PAR, filament, gas discharge, HID) according to some embodiments, or may be one or more blacklights (e.g., ultraviolet light) according to other embodiments, which may be replaced. In this embodiment, the protective sheet is attached around the surface of the surgical foot pedal device. The protective sheet may be transparent or translucent such that the foot pedal is still visible to the surgeon in some examples, or may be opaque in other examples.

Alternatively, the illuminating device(s) may be attached to various structures in the operating room. For example, the illuminating device(s) may be attached to a railing on the side of the operating room table or hung from a cord or cable off of a surface. The illuminating device(s) may be attached to an object using magnets or a plurality of clips. The illuminating device(s) may be attached to a bar and hung down from the side of a table using a bracket. Brackets are frequently readily available in an operating room and the illuminating device(s) may slip into one of these brackets.

The illuminating device(s) (e.g., LED bar) may be placed underneath a table or stand positioned over the foot pedal, with the light from the illuminating device(s) directed downwards to illuminate the area below the table or stand in examples where the illuminating device(s) emits visible light. In other embodiments, in which the illuminating device(s) emits ultraviolet light, the ultraviolet light may be directed onto the illuminated cover such that the illuminated cover is caused to fluoresce, thereby illuminating the foot pedal and/or frame. The illuminating device(s) may line the edges of the underside of the table or stand. The table or stand may have a clear top surface, or have an opened structure. A protective cover may be placed over part or the entirety of foot pedal and/or the lighted table or stand. In other examples, the illuminating device may hang from the side or back of the table or may be embedded within the table. In some examples, the table for retaining the plurality of illuminating devices may be reusable or disposable.

The illuminating device may be rigid such that the illuminating device may be configured to extend vertically from the surface of a platform or stand to illuminate a device placed on the platform. The illuminating device may extend any length (e.g. 3-10 inches) from the platform and may be angled in a number of different configurations to provide better visualization of the device, which in some examples may be a surgical device. In some embodiments, an illuminating device may extend vertically from the left and right back corners of a platform and have an additional illuminated device extension connecting the two bars of illuminating devices to provide a frame of illumination. In some configurations, the platform or stand may include a plurality of raised areas on the back and sides of the stand that are configured to hold the device in place.

The placement of the illuminating device may be contained and hidden underneath a divider (e.g. drapes) such that it does not interfere with the user, for example a surgeon operating in low light areas. However, the illuminating device should provide enough light to help adequately visualize the floor in the area right beneath the operating room table where the surgical device and the associated foot pedals would be located in examples where the illuminating device emits visible light, or should emit enough ultraviolet light so as to cause the illuminated cover to fluoresce sufficiently to visualize the foot pedal and/or frame.

Study Regarding Use of Illuminated Protective Cover

A study was conducted to determine whether illuminated foot pedals would improve the speed and accuracy of pedal activation during endoscopic procedures. The study was conducted at the Department of Urology at the Loma Linda University Medical Center at Loma Linda Calif., USA.

Introduction/Objectives:

Enduorological procedures such as percutaneous nephrostolithotomy (PCNL) commonly involve the use of multiple foot pedals to operate surgical instruments. Their visibility may be obscured in low-light operating room (OR) settings. The purpose of this study is to evaluate the impact of color-coded illumination on speed and accuracy of pedal activation in a simulated intraoperative setting.

Methods:

A simulated PCNL, using a C-arm, laser, and ultrasonic lithotripter (TM) in typical locations in a conventionally lit OR. Foot pedals were placed in three different positions underneath the table in front of the subject. Five attendings and five residents/fellows were instructed to activate the instruments by stepping on the foot pedals in a randomized sequence. Pedal position and orientation were randomized for each trial. Time to instrument activation, number of attempted pedal presses, number of missed attempts, and number of wrong pedal presses were recorded. 360 total instrument activations were conducted (18 instruments×10 subjects with and without color-coded pedal illumination). Each subject then completed a survey regarding their experiences and preferences with foot pedal illumination. Data was analyzed using the Mann Whitney U, Wilcoxon signed rank, and chi-square tests with $p<0.05$ indicating statistical significance.

Results:

Use of illuminated pedals was associated with decreased average activation time of all instruments together ($6.73\pm5.18$ s vs. $9.19\pm6.61$ s, $p<0.01$) as well as separately (c-arm: $3.53\pm2.02$ s vs. $5.20\pm3.87$ s, $p<0.01$; laser: $13.17\pm4.14$ s vs. $16.63\pm5.35$ s, $p<0.01$; UL: $3.58\pm1.51$ s vs. $5.99\pm3.62$ s, $p<0.01$). Illuminated pedals were associated with a decreased number of total attempted pedal presses ($27.5\pm8.7$ vs. $34.5\pm10.7$, $p<0.01$) and missed pedals ($2.6\pm3.2$ vs. $8.6\pm3.7$, $p<0.01$). The number of wrong pedals decreased with illumination but this finding did not reach statistical significance ($0.1\pm0.3$ vs. $1.3\pm2.5$, $p=0.08$). All subjects reported that illumination made the pedals easier to use and would recommend their use in regular practice ($p<0.01$). 9 of 10 (90%) subjects felt they made fewer mistakes, were more efficient, and felt a greater sense of security with the use of illuminated pedals ($p<0.01$ for each).

Conclusions:

Color-coded illumination improved speed and accuracy of pedal activation during enduorological surgery. A questionnaire revealed high surgeon satisfaction, with a greater perception of efficiency, security, and efficacy.

Study Regarding Use of Two Types of Illuminated. Foot Pedals

An additional study was conducted to compare the speed and accuracy of pedal activation with use of two types of illuminated foot pedals during endoscopic procedures. The study was conducted at the Department of Urology at the Loma Linda University Medical Center in Loma Linda, Calif., USA.

Introduction/Objectives:

Enduorological procedures such as percutaneous nephrostolithotomy (PCNL) commonly involve the use of multiple foot pedals to operate surgical instruments. Their visibility may be obscured in low-light operating room (OR) settings. The purpose of this study is to compare speed and accuracy, and evaluate dark adaptation and surgeon preference between two types of illuminated foot pedals and the operation of foot pedals in a dark and brightly lit simulated intraoperative setting.

Methods:

During a simulated PCNL, the foot pedals for a C-arm, holmium laser, and ultrasonic lithotripter (TM) were randomized to typical locations in an operating room (OR). Twenty participants activated the pedals in a randomized fashion using four different OR settings: dark room using blacklight illuminated pedals, dark room using glow stick illuminated pedals, dark room only, and brightly lit room only setting. Endpoints included time to pedal activation, number of attempted pedal presses, number of incorrect pedal presses, number of incomplete pedal presses, and surgeon preference between different pedal lighting schemes. Analysis was performed using a Mann-Whitney U Test, with $p<0.05$ considered statistically significant.

Results:

Glow sticks and blacklight fluorescent illumination for a foot pedal were both associated with decreased combined activation time as compared to no illumination (glow sticks: 6.77 s vs. 8.47 s, $p<0.001$; blacklight: 5.34 s vs. 8.47 s, $p<0.001$) and individual pedal activation time (glow sticks: C-arm: 3.60 s vs. 4.47 s, Laser: 13.43 s vs. 16.08 s, USL: 3.29 vs. 4.87, $p<0.001$; blacklight: C-arm: 2.57 s vs. 4.47 s, Laser: 11.02 s vs. 16.08 s, USL: 2.44 vs. 4.87, $p<0.001$). The blacklight system resulted in a statistically significant decrease in the number of attempted, incomplete, and incorrect pedal presses compared to xxxx (0.30 vs. 3.45, $p<0.001$; 1.25 vs. 7.75, $p<0.001$; 0.35 vs. 1.25, $p=0.035$, respectively) while demonstrating no difference in pedal activation time or inaccurate pedal presses compared to a brightly lighted room. Dark adaptation was significantly better for blacklight illuminated foot pedals compared to operation in a brightly lit room (values). Subjectively, 100% of participants preferred illuminated pedals for enduorological procedures compared to the low light setting, with 90% preferring the blacklight-fluorescent labeling system.

Conclusions:

Color-coded foot pedal illumination using blacklight illumination during simulated PCNL significantly improved the accuracy and efficiency of instrument activation compared to conventional dark operating room settings, while maintaining the benefits of dark adaptation for the surgeon.

Certain Terminology

"Foot pedal" is a broad term that is to be given its ordinary and customary meaning to a person of ordinary skill in the art (i.e., it is not to be limited to a special or customized meaning) and includes, without limitation, any mechanical device (e.g. button, pedal, switch, etc.) that may be engaged to activate a device, which in some embodiments may include a surgical device.

"Sheet" is a broad term that is to be given its ordinary and customary meaning to a person of ordinary skill in the art (i.e., it is not to be limited to a special or customized meaning) and includes, without limitation, any material that may be configured to cover a device and protect the device from moisture and other debris generated during the use of the device, for example to protect a surgical device from moisture and other debris generated during an operation.

"Illuminating device" is a broad term that is to be given its ordinary and customary meaning to a person of ordinary skill in the art (i.e., it is not to be limited to a special or customized meaning) and includes, without limitation, any device that can provide illumination to a surrounding area.

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that may be measured from side-to-side. Terms relating to shapes generally are not required to conform strictly to the mathematical definitions of the referenced structures, but can encompass structures that are reasonably close approximations.

Conditional language, such as "can," "could," "might," or "may," unless specifically stated otherwise, or otherwise understood within the context as used, is generally intended to convey that certain embodiments include or do not include certain features, elements, and/or steps. Thus, such conditional language is not generally intended to imply that features, elements, and/or steps are in any way required for one or more embodiments.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The terms "approximately," "about," and "substantially" as used herein represent an amount close to the stated amount that still performs a desired function or achieves a desired result. For example, in some embodiments, as the context may dictate, the terms "approximately," "about," and "substantially" may refer to an amount that is within less than or equal to 10% of the stated amount. The term "generally" as used herein represents a value, amount, or characteristic that predominantly includes or tends toward a particular value, amount, or characteristic.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" may include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

For expository purposes, the term "horizontal" as used herein is defined as a plane parallel to the plane or surface of the floor of the area in which the device being described is used or the method being described is performed, regardless of its orientation. The term "floor" may be interchanged with the term "ground." The term "vertical" refers to a direction perpendicular to the horizontal as just defined. Terms such as "above," "below," "bottom," "top," "side," "higher," "lower," "upper," "over," and "under" are defined with respect to the horizontal plane.

Overall, the language of the claims is to be interpreted broadly based on the language employed in the claims. The language of the claims is not to be limited to the non-exclusive embodiments and examples that are illustrated and described in this disclosure, or that are discussed during the prosecution of the application.

SUMMARY

Although illuminated covers have been disclosed in the context of certain embodiments and examples (e.g., foot pedals), this disclosure extends beyond the specifically disclosed embodiments to other alternative embodiments and/or uses of the embodiments and certain modifications and equivalents thereof. For example, any of the disclosed covers may be used on other types of devices, for example any surgical device that is used during a surgical procedure. Various features and aspects of the disclosed embodiments may be combined with or substituted for one another in order to form varying modes of the lighting of the foot pedals. The scope of this disclosure should not be limited by the particular disclosed embodiments described herein.

The methods disclosed herein include certain actions taken by a user; however, they can also include any third-party instruction of those actions, either expressly or by implication. For example, actions such as "attaching at least one illuminating device" include "instructing the attachment of at least one illuminating device."

Any of the covering assemblies described above may be provided as a kit. For example, the kit may include items such as a plurality of illuminating devices, a sheet, and a friction portion. In other examples, the kit may include also include adhesive to attach the plurality of illuminating devices or to secure the sheet.

Certain features that are described in this disclosure in the context of separate implementations can also be implemented in combination in a single implementation. Conversely, various features that are described in the context of a single implementation can also be implemented in multiple implementations separately or in any suitable subcombination. Although features may be described above as acting in certain combinations, one or more features from a claimed combination can, in some cases, be excised from the combination, and the combination may be claimed as any subcombination or variation of any subcombination.

Moreover, while operations may be depicted in the drawings or described in the specification in a particular order, such operations need not be performed in the particular order shown or in sequential order, and all operations need not be performed, to achieve the desirable results. Other operations that are not depicted or described may be incorporated in the example methods and processes. For example, one or more additional operations may be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying figures. The figures are drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components may be added, removed, and/or rearranged. Further, the disclosure herein of any particular feature, aspect, method, property, characteristic, quality, attribute, element, or the like in connection with various embodiments may be used in all other embodiments set forth herein. Additionally, any methods described herein may be practiced using any device suitable for performing the recited steps.

The present application is a Continuation and claims priority to and benefit of U.S. Non-Provisional application Ser. No. 16/169,651, titled "UV LIGHT ILLUMINATED SURGICAL COVERING APPARATUS AND METHOD," filed Oct. 24, 2018, which is a Continuation in Part of U.S. Non-Provisional application Ser. No. 16/048,260, titled "ILLUMINATED PROTECTIVE COVERING FOR FOOT PEDALS," filed Jul. 28, 2018, now U.S. Pat. No. 10,371,370, issued Aug. 6, 2019, which is a Continuation of U.S. Non-Provisional application Ser. No. 15/592,907, titled "ILLUMINATED PROTECTIVE COVERING FOR FOOT PEDALS," filed May 11, 2017, now U.S. Pat. No. 10,060,616, issued Aug. 28, 2018, which is a Continuation in Part of International Application No. PCT/US2015/061523, titled "ILLUMINATED PROTECTIVE COVERING," filed Nov. 19, 2015, which claims priority to and the benefit of U.S. Provisional Application No. 62/083,098, titled "FOOT PEDAL LIGHTS," filed Nov. 21, 2014; the full disclosure of each of these preceding applications is incorporated herein by reference in its entirety. U.S. Non-Provisional application Ser. No. 15/592,907, titled "ILLUMINATED PROTECTIVE COVERING FOR FOOT PEDALS," filed May 11, 2017, now U.S. Pat. No. 10,060,616, issued Aug. 28, 2018, also claims priority to and the benefit of U.S. Provisional Application No. 62/338,403, titled "ILLUMINATED PROTECTIVE COVERING," filed May 18, 2016, the full disclosure of which also is incorporated herein by reference in its entirety.

In summary, various embodiments and examples of illuminated protective covers have been disclosed. Although the assemblies have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments may be combined with, or substituted for, one another. Thus, the scope of this disclosure should not be limited by the particular disclosed embodiments described above, but should be determined only by a fair reading of the claims that follow.

What is claimed is:

1. A method for illuminating one or more medical procedure foot pedals, the method comprising:

positioning the one or more medical procedure foot pedals adjacent a floor surface and adjacent medical procedure equipment, the one or more medical procedure foot pedals positioned to activate one or more functions of the medical procedure equipment, each of the one or more medical procedure foot pedals having an optically brightened layer positioned on at least a portion of an upper surface thereof; and activating one or more ultraviolet (UV) illuminating devices to illuminate light therefrom and onto the one or more medical procedure foot pedals, such that the optically brightened layer fluoresces responsive to the activation of the one or more UV illuminating devices so as to facilitate visualization of the one or more medical procedure foot pedals when in use for a medical procedure.

2. The method of claim 1, wherein the method further comprises, prior to the step of positioning the one or more medical procedure foot pedals:

coating the at least a portion of the upper surface of each of the one or more medical procedure foot pedals with an optically brightened coating thereby to define the optically brightened layer.

3. The method of claim 1, wherein the method further comprises, prior to the step of positioning the one or more medical procedure foot pedals:

covering the at least a portion of the upper surface of each of the one or more medical procedure foot pedals with an optically brightened material layer so as to protect each of the one or more medical procedure foot pedals from at least one of debris and moisture during the medical procedure; and positioning a friction portion of the optically brightened material layer adjacent a lower surface of each of the one or more medical procedure foot pedals so as to reduce sliding of each of the one or more medical procedure foot pedals against the floor surface.

4. The method of claim 3, the method further comprising:

attaching the one or more UV illuminating devices to a frame, the frame comprising:
a bottom wall,
first and second walls extending upward from opposite lateral sides of the bottom wall, and
a third wall extending between the first and second walls and along a side of the bottom wall; and positioning the one or more medical procedure foot pedals in the frame such that the first, second, and third walls surround the one or more medical procedure foot pedals, the one or more medical procedure foot pedals comprising:
one or more medical procedure foot pedals, each of the one or more medical procedure foot pedals being arranged to transition from an initial position to a depressed position, and also being positioned to activate one or more medical functions of the medical procedure equipment when in the depressed position, the lower surface of each of the one or more medical procedure foot pedals being adapted to be positioned on the floor surface, wherein the one or more UV illuminating devices surround a majority of a perimeter of each of the one or more medical procedure foot pedals to illuminate light therefrom and onto the one or more medical procedure foot pedals such that the optically brightened layer fluoresces responsive to activation of the one or more UV illuminating devices.

5. The method of claim 4, wherein attaching each of the one or more UV illuminating devices to the frame comprises attaching each of the one or more UV illuminating devices to one or more of an inner surface of the frame and an outer surface of the frame, and wherein the optically brightened material layer is sufficiently flexible so as to substantially conform to a shape of the frame.

6. The method of claim 1, the method further comprising connecting each of the one or more UV illuminating devices to one or more of: (a) a portion of a perimeter of each of the one or more medical procedure foot pedals; and (b) the optically brightened layer.

7. A method for illuminating one or more medical procedure foot pedals, the method comprising:
providing an optically brightened layer to at least a portion of an upper surface of each of the one or more medical procedure foot pedals with an optically brightened layer, the optically brightened layer sufficiently flexible so as to substantially conform to a shape of each of the one or more medical procedure foot pedals;
positioning the one or more medical procedure foot pedals adjacent medical procedure equipment, the one or more medical procedure foot pedals configured to activate one or more functions of the medical procedure equipment;
positioning one or more ultraviolet (UV) illuminating devices adjacent the one or more medical procedure foot pedals; and
activating the one or more UV illuminating devices to illuminate light therefrom and onto the one or more medical procedure foot pedals, such that the optically brightened layer fluoresces responsive to activation of the one or more UV illuminating devices so as to facilitate visualization of the one or more medical procedure foot pedals when in use for a medical procedure.

8. The method of claim 7, the method further comprising coating the optically brightened layer with an optically brightened coating.

9. The method of claim 7, wherein the step of providing the optically brightened layer to at least a portion of the upper surface of each of the one or more medical procedure foot pedals comprises:
covering the at least a portion of the upper surface of each of the one or more medical procedure foot pedals with an optically brightened material layer so as to protect each of the one or more medical procedure foot pedals from at least one of debris and moisture during the medical procedure; and
positioning a friction portion of the optically brightened material layer adjacent a lower surface of each of the one or more medical procedure foot pedals so as to reduce sliding of each of the one or more medical procedure foot pedals against a floor surface.

10. The method of claim 9, the method further comprising:
attaching the one or more UV illuminating devices to a frame, the frame comprising:
a bottom wall,
first and second walls extending upward from opposite lateral sides of the bottom wall, and
a third wall extending between the first and second walls and along a side of the bottom wall; and
positioning the one or more medical procedure foot pedals in the frame such that the first, second, and third walls surround the one or more medical procedure foot pedals,
each of the one or more medical procedure foot pedals arranged to transition from an initial position to a depressed position, and also positioned to activate one or more medical functions of the medical procedure equipment when in the depressed position, the lower surface of each of the one or more medical procedure foot pedals adapted to be positioned on the floor surface,
wherein the one or more UV illuminating devices surround a majority of a perimeter of each of the one or more medical procedure foot pedals to illuminate light therefrom and onto the one or more medical procedure foot pedals such that the optically brightened layer fluoresces responsive to activation of the one or more UV illuminating devices.

11. The method of claim 10, wherein attaching each of the one or more UV illuminating devices to the frame comprises attaching each of the one or more UV illuminating devices to one or more of an inner surface of the frame and an outer surface of the frame.

12. The method of claim 7, the method further comprising connecting each of the one or more UV illuminating devices to one or more of: (a) a portion of a perimeter of each of the one or more medical procedure foot pedals; and (b) the optically brightened layer.

13. A system to visualize one or more medical procedure foot pedals when in use for a medical procedure, the system comprising:
one or more medical procedure foot pedals, the one or more medical procedure foot pedals positioned to transition from an initial position to a depressed position, and also positioned to activate one or more medical functions of medical procedure equipment when in the depressed position, a lower surface of each of the one or more medical procedure foot pedals being adapted to be positioned adjacent a floor surface and adjacent the medical procedure equipment;
one or more ultraviolet (UV) illuminating devices positioned to illuminate light therefrom and onto the one or more medical procedure foot pedals; and
an optically brightened layer positioned to cover at least a portion of an upper surface of each of the one or more medical procedure foot pedals, the optically brightened layer positioned to fluoresce responsive to activation of the one or more UV illuminating devices so as to facilitate visualization of the one or more medical procedure foot pedals when in use for the medical procedure.

14. The system of claim 13, wherein the optically brightened layer comprises an optically brightened coating.

15. The system of claim 13, wherein the optically brightened layer comprises an optically brightened material layer, the optically brightened material layer being positioned about each of the one or more medical procedure foot pedals so as to protect each of the one or more medical procedure foot pedals from at least one of debris and moisture during the medical procedure, and wherein the optically brightened material layer comprises a friction portion positioned adjacent the lower surface of each of the one or more medical procedure foot pedals so as to reduce sliding of each of the one or more medical procedure foot pedals against the floor surface.

16. The system of claim 15, wherein the optically brightened layer is sufficiently flexible so as to substantially conform to a shape of each of the one or more medical procedure foot pedals.

17. The system of claim 13, the system further comprising a frame positioned to receive the one or more medical procedure foot pedals.

18. The system of claim 17, wherein the frame comprises:
- a bottom wall;
- first and second walls extending upward from opposite lateral sides of the bottom wall; and
- a third wall extending between the first and second walls and along a side of the bottom wall,
- wherein the optically brightened layer is connected to the frame.

19. The system of claim 18, wherein each of the one or more UV illuminating devices is positioned on one or more of an inside surface of the frame and an outside surface of the frame.

20. The system of claim 18, wherein each of the one or more UV illuminating devices is positioned at an elevation above the bottom wall of the frame.

* * * * *